US008518422B2

(12) United States Patent
Mönks et al.

(10) Patent No.: US 8,518,422 B2
(45) Date of Patent: Aug. 27, 2013

(54) COSMETIC OR DERMATOLOGICAL PREPARATION COMPRISING A NUTRIENT MEDIUM PHASE

(75) Inventors: Monika Mönks, Schmitten (CH);
Sybille Ibanez, Uetikon am See (CH);
Carmen Evangelisti, Freienstein (CH);
Sven Gohla, Hamburg (DE)

(73) Assignee: La Prairie Group AG, Zurich (CH)

( * ) Notice: Subject to any disclaimer, the term of this patent is extended or adjusted under 35 U.S.C. 154(b) by 2325 days.

(21) Appl. No.: 11/068,052

(22) Filed: Mar. 1, 2005

(65) Prior Publication Data

US 2005/0287182 A1   Dec. 29, 2005

Related U.S. Application Data

(63) Continuation-in-part of application No. 10/967,232, filed on Oct. 19, 2004, which is a continuation of application No. PCT/EP2004/005533, filed on May 22, 2004.

(30) Foreign Application Priority Data

May 24, 2003   (DE) .................................. 103 23 510
Nov. 24, 2003  (DE) .................................. 103 55 110
Apr. 22, 2004  (DE) ........................ 10 2004 020 035

(51) Int. Cl.
*A61K 8/02*    (2006.01)
*A61K 8/65*    (2006.01)
*A61K 31/722*  (2006.01)
*A61K 31/726*  (2006.01)

(52) U.S. Cl.
USPC ................ 424/401; 514/54; 514/55; 514/801

(58) Field of Classification Search
USPC ......................................................... 424/401
See application file for complete search history.

(56) References Cited

U.S. PATENT DOCUMENTS

| | | | |
|---|---|---|---|
| 4,414,202 A | 11/1983 | Silvetti | |
| 4,605,623 A * | 8/1986 | Malette et al. | 435/377 |
| 4,619,827 A | 10/1986 | Bull et al. | |
| 4,708,861 A | 11/1987 | Popescu et al. | |
| 4,778,679 A | 10/1988 | Silvetti | |
| 4,784,854 A | 11/1988 | Seguin et al. | |
| 4,882,162 A * | 11/1989 | Ikada et al. | 424/444 |
| 5,106,949 A | 4/1992 | Kemp et al. | |
| 5,116,824 A | 5/1992 | Miyata et al. | |
| 5,166,187 A * | 11/1992 | Collombel et al. | 514/21 |
| 5,326,356 A | 7/1994 | Della Valle et al. | |
| 5,385,836 A * | 1/1995 | Kimura et al. | 435/177 |
| 5,461,030 A | 10/1995 | Lindenbaum | |
| 5,489,304 A | 2/1996 | Orgill et al. | |
| 5,534,416 A | 7/1996 | Millard et al. | |
| 5,591,709 A | 1/1997 | Lindenbaum | |
| 5,612,040 A | 3/1997 | Mason et al. | |
| 5,623,064 A | 4/1997 | Vournakis et al. | |
| 5,650,164 A | 7/1997 | Della Valle et al. | |
| 5,652,274 A | 7/1997 | Martin | |
| 5,658,331 A | 8/1997 | Della Valle et al. | |
| 5,676,948 A | 10/1997 | Bonte et al. | |
| 5,716,411 A | 2/1998 | Orgill et al. | |
| 5,759,570 A | 6/1998 | Arnold | |
| 5,830,507 A | 11/1998 | Armstrong | |
| 5,844,013 A | 12/1998 | Kenndoff et al. | |
| 5,906,937 A | 5/1999 | Sugiyama et al. | |
| 5,948,385 A | 9/1999 | Chapman et al. | |
| 6,043,089 A | 3/2000 | Sugiyama et al. | |
| 6,043,092 A | 3/2000 | Block | |
| 6,057,148 A | 5/2000 | Sugiyama et al. | |
| 6,106,855 A * | 8/2000 | Haynes et al. | 424/445 |
| 6,150,163 A | 11/2000 | McPherson et al. | |
| 6,231,836 B1 * | 5/2001 | Takhtalian et al. | 424/49 |
| 6,262,255 B1 | 7/2001 | Mares-Guia | |
| 6,372,494 B1 | 4/2002 | Naughton et al. | |
| 6,413,772 B1 | 7/2002 | Block | |
| 6,432,710 B1 | 8/2002 | Boss, Jr. et al. | |
| 6,492,503 B1 | 12/2002 | Kariya et al. | |
| 6,500,476 B1 * | 12/2002 | Martin et al. | 426/262 |
| 6,541,023 B1 | 4/2003 | Andre et al. | |
| 6,670,180 B2 | 12/2003 | Block | |
| 6,692,961 B1 | 2/2004 | Judd et al. | |
| 6,746,481 B1 * | 6/2004 | Larik et al. | 623/1.45 |
| 6,756,060 B1 | 6/2004 | Greenspan et al. | |
| 6,790,454 B1 * | 9/2004 | Abdul Malak et al. | 424/422 |

(Continued)

FOREIGN PATENT DOCUMENTS

DE   4233289   4/1994
DE   4308347   9/1994

(Continued)

OTHER PUBLICATIONS

Encyclopedia.com (Encyclopedia.com 2004. Dictionary of Biology, definition of Matrix, p. 1-5).*
Shahabeddin et al. (Skin Pharmacology, 1990, vol. 3, p. 107-114).*
Dulbecco's Modified Eagle's Medium (DMEM). Stemcell Technologies Inc. Jun. 2002.*
Lelong ("pH drift of "physiological buffers" and cluture media used for cell incubation during in vitro studies", J. Pharmacological and Toxicological Methods, 1998, 39, 203-210).*
Perreux et al. "Solvent-free preparation of amides from acids and primary amines under microwave irradiation" Tetrahedron, 2002, 58, 2155-2162.*
Shin, Y., et al., J. Appl. Polymer Sci. 2001, pp. 2495-2501.
U.S. Appl. No. 11/285,342, filed Nov. 23, 2005 and entitled "Tissue Culture Media Used As a Component of Cosmetics".

(Continued)

*Primary Examiner* — Kortney L Klinkel
(74) *Attorney, Agent, or Firm* — Abel Law Group, LLP

(57) ABSTRACT

A cosmetic or dermatological preparation that is obtainable by combining collagen and/or a derivative thereof, chitosan and/or a derivative thereof and glycosylaminoglycan and/or a derivative thereof with one or more selected substances. This Abstract is not intended to define the invention disclosed in the specification, nor intended to limit the scope of the invention in any way.

70 Claims, No Drawings

(56) References Cited

U.S. PATENT DOCUMENTS

| | | | |
|---|---|---|---|
| 7,118,746 B1 * | 10/2006 | Naughton et al. | 424/184.1 |
| 2002/0106703 A1 | 8/2002 | Sarvetnick et al. | |
| 2002/0155603 A1 | 10/2002 | Block | |
| 2004/0002055 A1 | 1/2004 | Andre et al. | |
| 2004/0028738 A1 * | 2/2004 | Huang et al. | 424/484 |
| 2004/0067584 A1 | 4/2004 | Judd et al. | |
| 2004/0153040 A1 * | 8/2004 | Martineau et al. | 604/304 |
| 2004/0166579 A1 | 8/2004 | Block | |
| 2005/0100588 A1 | 5/2005 | Kartheus et al. | |
| 2005/0249691 A1 * | 11/2005 | Monks et al. | 424/70.13 |
| 2006/0182701 A1 * | 8/2006 | Gohla et al. | 424/70.13 |

FOREIGN PATENT DOCUMENTS

| | | |
|---|---|---|
| DE | 4308445 | 9/1994 |
| DE | 4328190 | 3/1995 |
| DE | 10128685 | 12/2002 |
| EP | 0462626 | 12/1991 |
| JP | 0296078 | 12/1988 |
| JP | 2003-062057 | 3/2003 |
| WO | 98/04681 | 2/1998 |
| WO | 98/16629 | 4/1998 |
| WO | 98/22114 | 5/1998 |
| WO | 00/06608 A1 | 2/2000 |
| WO | 00/15167 | 3/2000 |
| WO | 00/78928 | 11/2000 |
| WO | 01/07605 | 2/2001 |

OTHER PUBLICATIONS

Shahabeddin L., et al. "Characterization of Skin Reconstructed on a Chitosan-Cross-Linked Collagen-Glycosaminoglycan Matrix" *Skin Pharmacology*, vol. 3, No. 2 (1990), pp. 107-114.

English Language Abstract of JP 2003062057. published Apr. 3, 2003.

Barnes, D.; Sato, G. "Methods for growth of cultured cells in serum-free medium" *Analytical Biochemistry*, 102 (2), 1980, pp. 255-270.

US 5,808,080, Sep.15, 1998, Mares-Guia (withdrawn).

English Language Abstract of WO 95/05857, published Mar. 2, 1995.

* cited by examiner

COSMETIC OR DERMATOLOGICAL PREPARATION COMPRISING A NUTRIENT MEDIUM PHASE

CROSS-REFERENCE TO RELATED APPLICATIONS

The present application is a continuation-in-part of U.S. patent application Ser. No. 10/967,232, filed Oct. 19, 2004, the entire disclosure whereof is expressly incorporated by reference herein, which is a continuation of International Application No. PCT/EP2004/005533, filed May 22, 2004, the entire disclosure whereof is expressly incorporated by reference herein, which claims priority under 35 U.S.C. §119 of German Patent Application Nos. 103 23 510.8, filed May 24, 2003, 103 55 110.7, filed Nov. 24, 2003, and 102004020035.1, filed Apr. 22, 2004.

BACKGROUND OF THE INVENTION

1. Field of the Invention

The present invention relates to a cosmetic or dermatological preparation which is obtainable by combining collagen and/or a derivative thereof, chitosan and/or a derivative thereof and glycosylaminoglycan and/or a derivative thereof with one or more substances which exhibit a beneficial effect when applied to healthy, injured or deseased skin. In one aspect, the preparation may comprise at least one nutrient medium phase for skin cells or corneal cells in combination with an aerogel or hydrogel matrix which comprises the above collagen/chitosan/glycosylaminoglycan combination. The invention further relates to cell culture media as aqueous phase in combination with the above matrix in synergistic use with polyurethanes which are employed for physiological wound healing or scar reduction.

2. Discussion of Background Information

Various circulations exist within the human body, such as the blood circulation, the lymphatic system and the intracellular and extracellular tissue fluids. The composition of the solvent "water" with its mineral and bioorganic constituents in these various "transport media" is approximately the same and is based, highly simplified, on salts, amino acids, vitamins, sugars, proteins and proteids, and trace elements. During evolution, our body has learnt to create within these fluids "communication networks" and nutritional strategies, and an equilibrium of catabolic to anabolic processes, which make the complex life of our multicellular body possible. In this environment, our body has learnt to construct from its "single individuals", the cells, a complicated but efficient network of direct and mediator-related contacts. These "communication pathways" function efficiently and harmlessly only if the natural dynamic equilibrium of our body, the so-called "homeostasis", is maintained. If cells are removed from the tissue assemblage or if the homeostasis in the tissue assemblage is impaired, it is no longer possible for individual cells to exist or for tissues to function healthily. The medical and biosciences have for decades looked for possibilities of cultivating tissues or individual cells in suitable environmental conditions outside the body. This was successful only when it was possible to simulate as perfectly as possible the living conditions in the body for the single cells or tissue constituents to be cultivated.

Thus, if cells are removed from intact tissue, they must be cultivated in environments which come as close as possible to the natural living conditions in the body. Requirements for this are supply and transport away of nutrients, and the presence of vital factors.

These environments are well-defined compositions of mineral and biomaterials which are known in science as cell culture media. Cell culture media are obtainable from suitable specialist retailers as powder or liquid media and have slightly different compositions depending on the nature of the cells or tissue constituents to be cultivated. Cell culture media are used in liquid form. With a suitable composition, they make it possible to maintain or even multiply microorganisms or cells in culture, i.e., outside the body.

In the course of tissue research it has been possible to identify and investigate the individual needs of cells and cells in intact tissues. In this connection, the ratio of mineral and bioorganic substances of a cell culture medium is slightly variable from cell type to cell type and must be ascertained accurately for optimized survival and growth. The composition of the cell culture medium always depends on the requirements of the cells to be grown. A distinction is made between synthetic media, whose ingredients are accurately known on the basis of pure substances, and complex media, whose exact composition may vary and is in part not accurately known. Cell culture media usually comprise, besides water, a carbon source and a nitrogen source, phosphate compounds and sulfur compounds, and minerals and, optionally, growth promoters and/or vitamins.

If the compositions of the media are suitable, the cells are able to multiply and produce the factors necessary for survival "in situ" by themselves.

In order to generate good growth of the cells, serum is frequently added to the cell culture media. The serum has a complicated composition and provides the cells with, inter alia, hormones, adhesion factors, and amino acids. Culture media which contain serum are, however, costly and do not allow thermal sterilization. One therefore usually tries to make do with media which contain no serum. Serum-free culture media make it possible to cultivate cells under controlled and defined conditions, so that unwanted effects due to variations in the serum composition are eliminated. In addition, contamination of the cell cultures with viruses and bacteria is reduced when using serum-free media.

It is known that skin cells can be kept alive particularly well-preserved and for long periods of time and can even be induced to grow and differentiate in one-, two- and three-dimensional cultures by optimizing the ingredients in the culture medium. It has also been possible to demonstrate that suitable media also make possible the production of growth factors in situ.

When there are extreme changes in the skin resulting from extensive burns or chills, the integrity and the functionality of the cutaneous tissue may be so impaired that the skin is no longer able to regenerate on its own. The body responds to such severe events with hyperthermia, massive release of mediators of inflammation and irritation, and with an enormous loss of fluid, which in the past has always and inevitably resulted in the death of people with severe burns. Burns and chills which have led to losses of cutaneous tissue can be compensated by skin transplants and thus the skin can be closed. However, this is successful only if sufficient remaining skin is available for transplantation. In cases of burns of more than 60% of the total cutaneous tissue, transplantation on its own is usually of no assistance. It is necessary to re-produce viable tissue from the remaining skin cells. In this connection, because of the rejection reactions between non-HLA-compatible tissues, it is not possible to take allogeneic skin or allogeneic skin cells. It is therefore necessary to form a new cutaneous tissue in situ from the remaining viable skin cells.

The hornified epidermis forms the protective shield of the skin. For this function to be optimally exercised it is necessary for the skin cells (keratinocytes) to pass through the process of so-called epidermal differentiation. After division of the cells in the basal layer, the keratinocytes migrate to the skin surface and undergo a number of changes during this, until they form the horny layer (stratum corneum) as dead, flat, anuclear corneocytes, and eventually are desquamated. During the epidermal differentiation there is formation of various proteins having specific functions. These include, inter alia, keratins, involucrin, filaggrin and transglutaminase. For optimal formation of the epidermis and the horny layer it is necessary for these proteins to be formed in coordinated fashion and in sufficient quantity.

Many cosmetics, skin care products or wound healing products which help to compensate or at least reduce the disorders of the skin are known in the prior art.

Thus, for example, geroderma is cosmetically treated primarily with vitamin A derivatives or hydroxy acids which lead, via stimulation of the proliferation of the basal cells in the epidermis, to a thickening of the epidermis and thus smoothing of the skin. More recent approaches consist of targeted replacement of the proteins which are absent or present in reduced quantity in dry skin or geroderma, or indirect intervention in the metabolic processes which are disturbed in dry skin or with increasing age, in order to normalize them. An example which may be mentioned here is stimulation of collagen synthesis with the aim of reducing wrinkles. In addition, for example, laminin, substances for prolonging the lifetime of skin cells and certain extracts for stimulating epidermal differentiation are employed. However, some of these are pharmacologically active substances with a high potential for side effects.

None of the preparations known from the prior art on their own enable the skin to reconstitute/regenerate itself without displaying unwanted side effects.

It would be advantageous to have available a preparation which enables the skin to regenerate itself without displaying unwanted side effects.

EP 296078, EP 462426 and U.S. Pat. Nos. 5,116,824, 6,541,023 and 5,808,050, the entire disclosures whereof are incorporated by reference herein, disclose preparations which comprise chitosans, collagens and glycosylaminoglycans. However, none of these documents discloses preparations which support the regeneration of the skin, lastingly improve the skin structure and help the skin to regain its elasticity and healthy appearance.

SUMMARY OF THE INVENTION

The present invention provides a cosmetic or dermatological preparation which is obtainable by combining certain substances. These substances comprise
  (a) collagen and/or a derivative thereof;
  (b) chitosan and/or acetylated chitosan with a degree of acetylation of up to about 50%;
  (c) at least one glycosylaminoglycan and/or a derivative thereof; and
  (d) at last one substance selected from amino acids (including the HCl salts thereof, preferably L-amino acids and even more preferred, essential amino acids), α-biotin, $(NH_4)_6Mo_7O_{24}$, adenine, $AlCl_3$, biotin, $CaCl_2$, calcium pantothenate, choline chloride, $CoCl_2$, $CrK(SO_4)_2$, $CuSO_4$, D-Ca pantothenate, $EDTA.Na_2$, $EDTA.Na_3$, $Fe(NO_3)_3$, $FeSO_4$, folic acid, glucose, $H_2SeO_3$, HEPES, hypoxanthine, insulin human, KCl, linoleic acid, lipoic acid, $MgCl_2$, $MnCl_2$, $MnSO_4$, myo-inositol, $Na_2HPO_4$, $Na_2SeO_3$, $Na_2SiO_3$, NaCl, $NaH_2PO_4$, $NaHCO_3$, sodium pyruvate, sodium acetate, $NH_4VO_3$, $NiCl_2$, nicotinamide, phenol red, polysorbate 80, putrescine, putrescine 2HCl, pyridoxine HCl, pyridoxal HCl, riboflavin, $SnCl_2$, thiamine HCl, thymidine, vitamin $B_{12}$, and $ZnSO_4$.

In one aspect of this preparation, the amino acids may comprise one or more substances selected from L-alanine, L-arginine, L-asparagine, L-aspartic acid, L-cysteine, L-cystine, glycine, L-glutamine, L-glutamic acid, L-histidine, L-isoleucine, L-leucine, L-lysine, L-methionine, L-phenylalanine, L-proline, L-serine, L-threonine, L-tryptophan, L-tyrosine, L-valine and the hydrochloride salts thereof.

In another aspect, at least two substances from the above group (d) may be employed, e.g., at least five, at least ten, at least twenty, at least fifty substances, or all substances from group (d).

In yet another aspect of the preparation of the present invention, the substances from group (d) may comprise at least one substance, e.g., at least two, three, four, five, six, seven or all of the substances selected from the group of glucose, folic acid, L-lysine, L-threonine, L-arginine, L-serine, L-histidine and glycine. In this regard, whenever in the present specification and the appended claims reference is made to an amino acid, this reference also includes the hydrochlorids salt of the amino acid. For example, "L-lysine" is intended to mean "L-lysine and/or L-lysine HCl".

In a still further aspect, at least one of the substances (a) and (b) may be of marine origin or of synthetic origin.

In another aspect, the collagen (a) may comprise one or more collagens selected from types 1, 3, 4 and 5 and/or the chitosan (b) may comprise chitosan having a molecular weight of from about 80,000 g/mol to about 15,000,000 g/mol and/or chitosan obtained from crustaceans and/or insects and/or the glycosylaminoglycan (c) may comprise chondroitin 4-sulfate and/or chondroitin 6-sulfate.

In another aspect, the substances (a) to (c) may be employed in a total amount of from about 0.0005% to about 50% by weight, based on the total weight of the preparation, e.g., in a total amount of from about 0.0015% to about 30% by weight, from about 0.005% to about 10% by weight, from about 0.01% to about 1% by weight, or from about 0.015% to about 0.1% by weight.

In another aspect of the preparation of the present invention, the weight ratio of the substances (a) and (c) may be from about 35:1 to about 3:1, e.g., from about 20:1 to about 6:1, or from about 10:1 to about 8:1.

In yet another aspect of the preparation, the weight ratio of the substances (a) and (b) may be from about 10:1 to about 1.5:1, e.g., from about 7:1 to about 2.5:1, or from about 5:1 to about 3.5:1.

In a still further aspect, the weight ratio of the substances (b) and (c) may be from about 10:1 to about 1:1, e.g., from about 5:1 to about 1.5:1, or from about 3:1 to about 2:1.

In another aspect, the preparation may comprise one or more skin cell culture media. For example, the skin cell culture media may comprise DMEM/HAM F12 (1:1) and/or MCDB 153. In yet another aspect, the preparation may comprise a nanosponge matrix and/or a microsponge matrix formed by the substances (a) to (c), which matrix has been reconstituted in cell culture media. By way of non-limiting example, the cell culture media may be selected from physiological saline solution, nutrient media and complete media for culturing primary body cells, e.g., culture media for primary fibroblasts and keratinocytes. The complete media may, for example, be supplemented with serum substitutes.

In another aspect, the preparation may further comprise one or more of a citrate buffer, Q10, alpha-glucosyl rutin, Zn orotate, carnitine, creatine and taurine and/or one or more alpha-hydroxy acids.

In another aspect, the preparation may further comprise water, for example, at least about 30% by weight of water, based on the total weight of the preparation, e.g., at least about 40%, at least about 50%, at least about 60%, at least about 70%, at least about 80%, at least about 90%, or at least about 95% by weight of water.

The present invention also provides a cosmetic or dermatological product which is selected from an aqueous gel, an O/W emulsion, a W/O/W emulsion, a W/O emulsion, a microemulsion and a cosmetic stick and which comprises the preparation of the present invention, including the various aspects thereof.

The present invention further provides a cosmetic or dermatological product which is selected from an aqueous surfactant preparation, an emulsion, an ointment, a cream, a gel, a dusting powder, a mask, a matrix bandage, a gel bandage, a foam preparation and an aerosol preparation and comprises the preparation of the present invention, including the various aspects thereof.

The present invention also provides an article which is selected from a wound covering, a skin covering, a patch, a pad, a tissue and a bandage and comprises the preparation of the present invention, including the various aspects thereof.

The present invention further provides a polyurethane matrix which comprises the preparation of the present invention, including the various aspects thereof.

The present invention also provides a cosmetic or dermatological preparation which is obtainable by combining various substances, which substances comprise
(a) collagen and/or a derivative thereof;
(b) chitosan and/or acetylated chitosan with a degree of acetylation of up to 50%;
(c) at least one glycosylaminoglycan and/or a derivative thereof; and
(d) at last four substances selected from glucose, folic acid, L-lysine, L-threonine, L-arginine, L-serine, L-histidine and glycine; and
(e) at least 50% by weight of water, based on the total weight of the preparation.

In this preparation, the substances (a) to (c) are employed in a total amount of from about 0.005% to 10% by weight, based on the total weight of the preparation, the substances (a) and (b) are employed in a weight ratio of from about 6:1 to about 3:1 and the substances (a) and (c) are employed in a weight ratio of from about 15:1 to about 7:1.

In one aspect, the preparation may comprise all of glucose, folic acid, L-lysine, L-threonine, L-arginine, L-serine, L-histidine and glycine.

In another aspect, the substances (a) to (c) may be employed in a total amount of from about 0.015% to about 0.1% by weight and/or the weight ratio of substances (a) and (c) may be from about 10:1 to about 8:1 and/or the weight ratio of substances (a) and (b) may be from about 5:1 to about 3.5:1 and/or the weight ratio of substances (b) and (c) may be from about 3:1 to about 2:1.

In yet another aspect of the preparation, one or more substances selected from α-biotin, $(NH_4)_6Mo_7O_{24}$, adenine, $AlCl_3$, biotin, $CaCl_2$, calcium pantothenate, choline chloride, $CoCl_2$, $CrK(SO_4)_2$, $CuSO_4$, D-Ca pantothenate, $EDTA.Na_2$, $EDTA.Na_3$, $Fe(NO_3)_3$, $FeSO_4$, $H_2SeO_3$, HEPES, hypoxanthine, insulin human, KCl, linoleic acid, lipoic acid, $MgCl_2$, $MnCl_2$, $MnSO_4$, myo-inositol, $Na_2HPO_4$, $Na_2SeO_3$, $Na_2SiO_3$, NaCl, $NaH_2PO_4$, $NaHCO_3$, sodium pyruvate, sodium acetate, $NH_4VO_3$, $NiCl_2$, nicotinamide, phenol red, polysorbate 80, putrescine, putrescine 2HCl, pyridoxine HCl, pyridoxal HCl, riboflavin, $SnCl_2$, thiamine HCl, thymidine, vitamin $B_{12}$, $ZnSO_4$, L-alanine, L-asparagine, L-aspartic acid, L-cysteine, L-cystine, glycine, L-glutamine, L-glutamic acid, L-histidine, L-isoleucine, L-leucine, L-methionine, L-phenylalanine, L-proline, L-tyrosine and L-valine may additionally be employed therein. In a still further aspect of the preparation, the collagen may comprise one or more collagens selected from types 1, 3, 4 and 5 and/or the chitosan may comprise chitosan having a molecular weight of from about 80,000 g/mol to about 15,000,000 g/mol and/or the glycosylaminoglycan may comprise chondroitin 4-sulfate and/or chondroitin 6-sulfate.

In another aspect, the preparation may comprise one or more cell culture media.

The present invention also provides a skin care method which comprises applying to the skin the preparation of the present invention, including the various aspects thereof.

The present invention further provides a skin treatment method which comprises applying to injured or diseased skin the preparation of the present invention, including the various aspects thereof.

The present invention also provides a wound management or wound healing method which comprises applying to a wound the preparation of the present invention, including the various aspects thereof. For example, the preparation may be comprised in a wound covering, e.g., a wound covering that comprises a polyurethane.

The present invention also provides a method of generating a complete partial skin. This method comprises applying the preparation of the present invention, including the various aspects thereof, to the surface of a body from which skin has been removed.

The present invention further provides a method of preventing or reducing scar tissue, which method comprises applying to a wound the preparation of the present invention, including the various aspects thereof.

The present invention also provides a process for preparing a cosmetic or dermatological preparation which comprises collagen and/or a derivative thereof, chitosan and/or an acyl derivative thereof with a degree of acetylation of up to 50%, and a glycosylaminoglycan and/or a derivative thereof. This process comprises
(a) providing a solution comprising water and collagen and/or a derivative thereof;
(b) adding chitosan and/or acetylated chitosan with a degree of acetylation of up to 50% to the solution of (a); and
(c) adding a glycosylaminoglycan and/or a derivative thereof to the mixture of (b) to form a further mixture;
(d) combining at least one substance selected from an amino acids, α-biotin, $(NH_4)_6Mo_7O_{24}$, adenine, $AlCl_3$, biotin, $CaCl_2$, calcium pantothenate, choline chloride, $CoCl_2$, $CrK(SO_4)_2$, $CuSO_4$, D-Ca pantothenate, $EDTA.Na_2$, $EDTA.Na_3$, $Fe(NO_3)_3$, $FeSO_4$, folic acid, glucose, $H_2SeO_3$, HEPES, hypoxanthine, insulin human, KCl, linoleic acid, lipoic acid, $MgCl_2$, $MnCl_2$, $MnSO_4$, myo-inositol, $Na_2HPO_4$, $Na_2SeO_3$, $Na_2SiO_3$, NaCl, $NaH_2PO_4$, $NaHCO_3$, sodium pyruvate, sodium acetate, $NH_4VO_3$, $NiCl_2$, nicotinamide, phenol red, polysorbate 80, putrescine, putrescine 2HCl, pyridoxine HCl, pyridoxal HCl, riboflavin, $SnCl_2$, thiamine HCl, thymidine, vitamin $B_12$, and $ZnSO_4$ with one or more of the solution and mixtures of (a) to (c).

In one aspect of this process, the solution of (a) may comprise one or more cell culture media.

In another aspect, the glycosylaminoglycan may comprise chondroitin 4-sulfate and/or chondroitin 6-sulfate and/or the collagen may comprise one or more collagens selected from types 1, 3, 4 and 5 and/or the chitosan may comprise chitosan having a molecular weight of from about 80,000 g/mol to about 15,000,000 g/mol.

In yet another aspect, the process may further comprise lyophilizing the mixture of (c) to provide an aerogel. Further, the aerogel may be converted into a hydrogel by introducing the aerogel into an aqueous phase, an active ingredient phase and/or a culture media phase of the cosmetic or dermatological preparation. In another aspect, the aerogel may be processed into a polyurethane matrix.

Regarding the weight ratios of the components (a) to (d) of the preparation of the present invention, it is noted that the weight ratio (a):(b) will usually be not higher than about 10:1, e.g., not higher than about 8:1, not higher than about 7:1, not higher than about 6:1, or not higher than about 5:1, and will usually be not lower than about 1.5:1, e.g., not lower than about 2:1, not lower than about 2.5:1, not lower than about 3:1, or not lower than about 3.5:1.

The weight ratio (a):(c) will usually be not higher than about 35:1, e.g., not higher than about 30:1, not higher than about 25:1, not higher than about 20:1, not higher than about 15:1, or not higher than about 10:1, and will usually be not lower than about 4:1, e.g., not lower than about 5:1, not lower than about 6:1, not lower than about 7:1, or not lower than about 8:1.

The weight ratio (b):(c) will usually be not higher than about 10:1, e.g., not higher than about 8:1, not higher than about 6:1, not higher than about 5:1, not higher than about 4:1, or not higher than about 3:1, and will usually be not lower than about 1:1, e.g., not lower than about 1.5:1, or not lower than about 2:1.

Regarding the weight ratio of the total substances [(a)+(b)+(c)] and the substances of group (d), the ratio [(a)+(b)+(c)]:(d) will usually be from about 100:1 to about 1:100. When one or more substances from the group glucose, folic acid, L-lysine, L-threonine, L-arginine, L-serine, L-histidine and glycine are employed, the weight ratio of [(a)+(b)+(c)] and the total amount of these substances (d) will usually be not higher than about 30:1, e.g., not higher than about 20:1, or not higher than about 10:1, and not lower than about 1:20, e.g., not lower than about 1:15, or not lower than about 1:10.

In addition to the use of glucose, folic acid, L-lysine, L-threonine, L-arginine, L-serine, L-histidine and/or glycine, the use of L-tryptophan and/or calcium pantothenate for the manufacture of the preparation of the present invention may also be of particular advantage.

The substances (a) to (c) will usually be employed in a total amount of from about 0.00001% by weight to about 99% by weight, based on the total weight of the preparation. However, frequently the total amount will be not higher than about 50% by weight, e.g., not higher than about 30% by weight, not higher than about 10% by weight, not higher than about 1% by weight, or not higher than about 0.1% by weight, but not lower than about 0.0001% by weight, e.g., not lower than about 0.0015% by weight, not lower than about 0.005% by weight, not lower than about 0.01% by weight, or not lower than about 0.015% by weight.

It has unexpectedly been found that a cosmetic and/or dermatological preparation which comprises a mixture that is obtainable by combining collagen (and/or a collagen derivative), chitosan (and/or acetylated chitosan with a degree of acetylation not exceeding about 50%) and a glycosylaminoglycan (and/or a derivative thereof with one or more (e.g., all) of the substances from group (d) is particularly effective in enabling the skin to reconstitute itself without displaying unwanted side effects to any substantial extent.

Preparations according to the present invention which additionally comprise one or more skin cell culture media, preferably at least DMEM/HAM F12 (1:1) and/or MCDB 153, are particularly advantageous. In addition, all culture media which permit the culture of healthy differentiated skin (3-D models) and, in particular, media which may be used to culture primary fibroblasts and/or keratinocytes and make complete reconstitution of the skin possible are contemplated as culture media for use in the present invention. Serum substitutes for serum-free cell cultures may also advantageously be used, although they are not indispensible.

A particularly advantageous combination according to the present invention comprises cell-nourishing culture media, preferably media for cultivating skin cultures or corneal cultures of all types, with a cellular matrix that comprises collagens, acetylated chitosans with a degree of acetylation of up to about 50%, preferably up to about 40%, and chondroitin sulfates. This combination by itself, or mixed with a cosmetic preparation or incorporated into a natural or synthetic polymer matrix such as, e.g., a polyurethane matrix is extremely efficient with respect to skin regeneration/reconstitution, skin care and wound healing.

The preparation of the present invention makes it possible to regenerate skin or partial skin from individual cells (dermis and epidermis) to form a gel matrix that is precultured in vitro, to transfer this matrix to damaged tissue for complete skin renewal and/or the prevention or reduction of scar tissue associated with wound healing. The preparation of the present invention further provides the ideal environment (matrix) for renewing the skin on topical application.

A process for the preparation of a matrix that may be used in the present invention is described in, e.g., EP 296078, mentioned above.

It has unexpectedly been found that it is possible to obtain the matrix described in EP 296078 by using entirely marine and/or synthetic raw material sources and that the results are the same as those obtainable with the matrix of EP 296078.

In one aspect, the preparation of the present invention may be described as comprising a primary microporous or nanoporous matrix which preferably comprises marine collagens selected from the group of type 3, type 1, type 4 and/or type 5 or blends thereof, chitosans, preferably with a molecular weight of from about 80,000 D to about 15,000,000 D and with a degree of acetylation of from about 5% to about 50%, blended with a mixture of chondroitin 4- and 6-sulfates, which are preferably employed in an amount of from about 3% to about 15% by weight based on the amount of the employed collagens. The matrix can be imagined to be in the form of a microtubular or nanotubular sponge. On lyophilization, the composition of the described molecules generates a nano- or microsponge (matrix).

The matrix may be composed of an aerogel prepared by lyophilization, which matrix may be introduced into the aqueous phases, active ingredient phases and/or culture media phases of finished cosmetic or dermatological preparations. In this case, the aerogel may be converted into a hydrogel, or may be processed as aerogel, for example, together with (and/or into) a polyurethane matrix or a silicone matrix.

It has been shown that the preparation according to the present invention, especially in combination with cell culture media, results in advantages in the morphology and growth rate of primary human keratinocytes and fibroblasts from young and old donors in vitro. In principle, all growth and maintenance media are suitable for this purpose, but those which are adapted to the requirements of skin cells and enable the construction of "new skin" from individual dermis and/or epidermis cells in the described matrix usually afford the best results.

Application studies have shown that irritated skin is soothed on treatment with the matrix according to the present invention. In this regard, it is particularly advantageous if the collagen, chitosan and glycosylaminoglycan ingredients for use in the preparation of the present invention are employed in a balanced ratio to one another, especially as described in EP 296078. In other words, formation of a micro- or nanotubular aerogel and retention of this structure in a cosmetic preparation or skin covering will usually be possible only within certain ranges of ratios of the specific active ingredients.

In this case, the stationary biopolymer phase with the disperse phase(s) composed of physiological saline solution, minimal media or complete media is converted into a hydrogel phase. The matrix components of the present invention (i.e., collagen, chitosan, glycosylaminoglycan) result in an advantageous hydrogel phase. An individual active ingredient or only two of the active ingredients alone, or the combination of active ingredients in non-advantageous proportions do not result in desirable effects, for example, a favorable interaction with the cell culture media as aqueous phase, or with polyurethane or silicone matrices.

A preferred weight ratio of the collagen and chitosan components is from about 90:10 to about 60:40, in particular from about 85:15 to about 75:25.

Collagen is a designation for a family of long-fiber, linear-colloidal, high molecular weight scleroproteins of the extracellular matrix which occur in connective tissue (e.g. skin, cartilage, tendons, ligaments, blood vessels), in osseine (the protein-containing base substance of bone) and in dentin together with proteoglycans. They are regarded as the most common animal proteins in terms of quantity, with a proportion of 25-30%. A mutual anchoring of the collagen fibers and of the cells is produced by fibronectin, which is able to bind collagen and other constituents of the extracellular matrix, but also becomes attached to receptors on cell surfaces. The composition of the collagens may vary depending on the origin. Collagens of types I to XIV are known, but only types I-III, V and XI have the described fiber structure.

When applied to the skin, advantages of the preparation of the present invention include:
  Supporting the regeneration process of the skin
  Providing a optimum environment for the skin
  Instrumental in improving the skin structure
  Soothing of skin irritations
  Improving the entire condition of the skin
  Improving the appearance of the skin substantially
  Helping the skin to regain its elasticity and healthy impression The preparation (matrix) of the present invention may be a component of, by way of non-limiting example, aqueous gels, emulsions of the O/W, W/O/W or W/O type, microemulsions or cosmetic stick products and can thus be marketed in conventional cosmetic application forms.

In addition, the preparation of the present invention may be comprised in skin coverings, patches, pads, tissues or bandages. In this regard, polyurethane-based wound coverings are of particular interest.

An in-home-use application of the preparation of the present invention is possible, too. By way of non-limiting example, in the form of an aerogel, the matrix can be placed on the wound or the part of skin that is to be treated. The constituents of the matrix of the invention are biological polymers which can, through a specific mixing ratio, be converted into a stable aerogel and can even be reconstituted as stable hydrogel. It has been show experimentally that this gel matrix, when placed on a wound, is capable of producing complete healing skin from individual skin cells. Advantages were found and demonstrated for the preparation of the present invention for cell regeneration and proliferation of primary skin cells of the keratinocyte and fibroblast type. It is also possible through the glycosylaminoglycan, chitosan and collagen matrix interacting with the skin cells, in particular in the 3-D skin models, to induce the production of elastin, fibrillin and further biomarkers which are responsible for the quality of a healthy skin. It further is possible, through the interaction of matrix molecules, as described above, and the cell culture media, to markedly improve the reticular interlocking of the epidermis in the dermis. It is thus possible, through the preparation of the invention in interaction with the culture media, to achieve ideal regeneration of complete skin from only a few skin cells, and supply a pre-existing skin with the ideal healthy growth environment and nutrient factors. In interaction with polyurethane components, skin regeneration can be optimized under semi- or occlusive conditions, which helps to normalize in particular, keloids and other scars.

The process of producing the described matrix may advantageously comprise the addition of optionally acetylated chitosan to a collagen/water solution which may also comprise cell culture media, and the subsequent addition of a glycosylaminoglycan, preferably at least chondroitin 4-sulfate and/or chondroitin 6-sulfate.

The preferred proportions of the active ingredients of the preparation according to the present invention allow sustained or controlled release of active agents such as, e.g., Q10, retinol, AHA (alpha-hydroxy acids), etc. and, in addition, may reduce or eliminate the side effects of these agents.

The most important alpha-hydroxy acids include glycolic acid, lactic acid, citric acid, tartaric acid, malic acid and salicylic acid. These acids contribute to an ablation of keratinized furfur. The skin immediately becomes smoother, fresher and softer. Pigmental moles become lighter.

Coenzyme Q10 or ubiquinone is present in almost all organisms and plays an important role in cell metabolism. Q10 also is an effective antioxidant, scavenges free radicals and stabilizes cell membranes. Thereby Q10 keeps the cells intact, functional and alive.

The term "skin cell culture medium" is intended to encompass all liquid, powdered or solid media in or on which individual cells can multiply or be cultivated. Those of skill in the art distinguish between purifying media such as, e.g., phosphate-buffered saline solution, minimal maintenance media and so-called complete media, in which cells are healthy and metabolically active. Complete media may be provided with growth factors from animal serum or so-called synthetic serum substitutes in order to improve the growth of specific cells or make same possible at all. For every cell type, but especially the culture of primary cells, there are media and media blends which support the growth, differentiation or metabolism of specific cells particularly well.

The combination according to the present invention of collagens, chitosans and glycosylaminoglycans (e.g., chondroitin sulfates) may be blended with all purifying, minimal or complete media, but particularly advantageously with complete media which have been composed for culturing skin cells and serve in particular as nutrient media for primary human fibroblasts and keratinocytes and which, as nutrient media, make it possible for the dermis to be regenerated from individual fibroblasts, or for the epidermis to be regenerated from individual keratinocytes. The skin cell culture media which are employed according to the present invention are thus particularly suitable for cultivating skin cells. Particular preference is given to skin cell culture media which are described as being suitable, in the composition of their individual ingredients, for the following purposes:
- culture of fibroblast cells
- culture of keratinocyte cells
- co-cultures of keratinocytes and fibroblasts
- co-cultures of fibroblasts/keratinocytes and further skin-relevant cells such as immune cells, melanocytes etc.
- culture media for generating three-dimensional skin models.

The media which are preferably employed according to the present invention can act on keratinocyte/fibroblast mixed cultures and 3-D skin models.

It has surprisingly been found that cosmetic or dermatological compositions which comprise the mixture according to the present invention of biomolecules and skin cell culture media are able in or on the human skin itself to activate or simulate the mechanisms which the skin uses for homeostasis and healthy autopoiesis. In this regard, the mixtures of fibroblast- or keratinocyte-relevant growth media may be employed directly or in suitable vesicle technologies, and may be used for medical/pharmaceutical purposes and cosmetic purposes. In particular, so-called serum-free media have proved to be advantageous when the cell fraction of the primary keratinocytes and primary fibroblasts is to be positively influenced in the sense of optimized homeostasis.

The use of the skin-relevant culture media in interaction with the matrix biomolecules brings about autologous, healthy and individual regeneration of deficient skin functions in vitro, ex vivo and in vivo. It is thus possible for regeneration of the skin, skin tautness or else simply only the contribution to skin care to be significantly improved.

In principle, all skin cell culture media are suitable for use in cosmetic preparations. Particularly suitable skin cell culture media are those employed in the literature for cultivating skin cells or skin-relevant cells, for treating skin irritations and burns. In particular, media for cultivating remaining cells after extensive burns show an extremely advantageous effect after application of the topical preparations.

Skin cell culture media which are particularly advantageous according to the present invention include media which permit neogenesis of fibroblasts or keratinocytes alone or in mixed cultures and/or which reduce the formation and passaging of non-benign cells.

The skin cell culture media DMEM/HAM F12 (1:1) and MCDB 153 are particularly suitable for use in the present invention, in particular, for use in cosmetic preparations.

According to Barnes D. and Sato G., Anal. Biochem. 102, 255 [1980], the entire disclosure whereof is incorporated by reference herein, DMEM/HAM F12 (1:1) is a 1:1 mixture where the nutrient content of HAM F12 medium is increased through addition of Dulbecco's MEM (DMEM=Dulbecco's Modified Eagles Medium). This medium is the basis for cultivating cell lines for human proteins such as, for example, erythropoetin.

DMEM/HAM F12 (1:1) medium has the following composition (in mg/L):

| | | | |
|---|---|---|---|
| NaCl | 6999.5 | L-Leucine | 59 |
| KCl | 311.8 | L-Lysine HCl | 91.25 |
| $Na_2HPO_4$ | 71 | L-Methionine | 17.24 |
| $NaH_2PO_4$—$H_2O$ | 62.5 | L-Phenylalanine | 35.5 |
| $MgSO_4$—$7H_2O$ | 100 | L-Proline | 17.25 |
| $MgCl_2$—$6H_2O$ | 61 | L-Serine | 26.25 |

-continued

| | | | |
|---|---|---|---|
| $CaCl_2$ | 116.61 | L-Threonine | 53.5 |
| $Fe(NO_3)_3$—$9H_2O$ | 0.05 | L-Tryptophan | 9 |
| $FeSO_4$—$7H_2O$ | 0.417 | L-Tyrosine | 38.7 |
| $CuSO_4$—$5H_2O$ | 0.00125 | L-Valine | 52.85 |
| $ZnSO_4$—$7H_2O$ | 0.432 | | |
| D-Glucose | 3151 | Choline chloride | 9 |
| $NaHCO_3$ | 2438 | α-Biotin | 0.00365 |
| Na Pyruvate | 55 | Folic acid | 2.65 |
| Phenol red | 12.5 | D-Ca pantothenate | 2.24 |
| myo-Inositol | 12.6 | | |
| L-Alanine | 4.5 | Nicotinamide | 2.02 |
| L-Arginine HCl | 147.5 | Pyridoxcal HCl | 2 |
| L-Asparagine-$H_2O$ | 7.5 | Pyridoxine HCl | 0.031 |
| L-Aspartic acid | 6.65 | Riboflavin | 0.22 |
| L-Cysteine HCl | 15.75 | Thiamine HCl | 2.17 |
| L-Cystine | 24 | Vitamin $B_{12}$ | 0.68 |
| L-Glutamine | 365.3 | Hypoxanthin | 2.05 |
| L-Glutamic acid | 7.35 | Thymidine | 0.37 |
| Glycine | 18.75 | Lipoic acid | 0.11 |
| L-Histidine HCl—$H_2O$ | 31.5 | Linoleic acid | 0.042 |
| L-Isoleucine | 54.5 | Putrescine 2HCl | 0.081 |

According to Barnes D. and Sato G., Anal. Biochem. 102, 255 [1980], MCDB 153 medium is employed for cultivating human keratinocytes. Further, as minimal medium PBS, phosphate-buffered saline, with pH values of from 3.5 to 8.

MCDB 153 medium has the following composition (mg/L):

| | | | |
|---|---|---|---|
| NaCl | 7599 | Choline chloride | 13.96 |
| KCl | 111.83 | Putrescine | 0.1611 |
| Sodium acetate-$3H_2O$ | 500 | Vitamin $B_{12}$ | 4.07 |
| $Na_2HPO_4$—$7H_2O$ | 536.2 | Biotin | 0.0146 |
| $MgCl_2$—$6H_2O$ | 122 | Calcium pantothenate | 0.258 |
| $CaCl_2$—$2H_2O$ | 4.411 | Nicotinamide | 0.03663 |
| Glucose | 1081 | Pyridoxine HCl | 0.06171 |
| Sodium pyruvate | 55 | Thiamine HCl | 0.3373 |
| $NaHCO_3$ | 1176 | Adenine | 24.32 |
| Phenol red | 1.317 | myo-Inositol | 18.02 |
| HEPES | 6600 | Lipoic acid | 0.2063 |
| Thymidine | 0.7266 | | |
| L-Alanine | 8.91 | Folic acid | 0.79 |
| L-Arginine-HCl | 210.7 | Riboflavin | 0.03764 |
| L-Asparagine | 15.01 | | |
| L-Aspartic acid | 3.99 | $CuSO_4$—$5H_2O$ | 0.0002496 |
| L-Cysteine HCl—$H_2O$ | 42.04 | $FeSO_4$—$7H_2O$ | 1.39 |
| L-Glutamine | 877.2 | $MnSO_4$—$5H_2O$ | 0.000241 |
| L-Glutamic acid | 14.71 | $(NH_4)_6Mo_7O_{24}$—$4H_2O$ | 0.001236 |
| Glycine | 7.51 | $NiCl_2$—$6H_2O$ | 0.0001188 |
| L-Histidine HCl—$H_2O$ | 16.77 | $H_2SeO_3$ | 0.003869 |
| L-Isoleucine | 1.968 | $Na_2SiO_3$—$9H_2O$ | 0.1421 |
| L-Leucine | 65.6 | $SnCl_2$—$2H_2O$ | 0.0001128 |
| L-Lysine-HCl | 18.27 | $NH_4VO_3$ | 0.000585 |
| L-Methionine | 4.476 | $ZnSO_4$—$7H_2O$ | 0.144 |
| L-Phenylalanine | 4.956 | | |
| L-Proline | 34.53 | | |
| L-Serine | 63.06 | | |
| L-Threonine | 11.91 | | |
| L-Tryptophan | 3.06 | | |
| L-Tyrosine | 2.718 | | |
| L-Valine | 35.13 | | |

The advantage of the DMEM/HAM F12 (1:1) and MCDB 153 media is that they are particularly selected and suitable in cosmetic or dermatological preparations for the cultivation of monolayer, two-dimensional and organotypical skin models, and permit the in vitro and ex vivo stimulation and/or retention of skin-specific biofunctions.

Additionally, it may be advantageous to add to the media solutions of the following compositions A and B as serum substitutes:

| Solution A | | Solution B | |
|---|---|---|---|
| Components (1000x) | μM | Components (1000x) | μM |
| $FeSO_4$—$7H_2O$ | 3000 | Insulin human in 0.01 M HCl | 86 |
| $ZnSO_4$—$7H_2O$ | 3000 | | |
| $CoCl_2$—$6H_2O$ | 1000 | | |
| $CuSO_4$—$5H_2O$ | 10 | | |
| $Na_2SeO_3$ | 10 | | |
| $AlCl_3$—$6H_2O$ | 5 | | |
| $CrK(SO_4)_2$—$12H_2O$ | 1.4 | | |
| $NiCl_3$—$6H_2O$ | 1 | | |
| $MnCl_2$—$4H_2O$ | 1 | | |
| $EDTA.Na_2$—$2H_2O$ | 30000 | | |
| Polysorbate 80 VG | 3820 | | |

According to the literature, the liquid media are usually prepared by using high-purity, pyrogen-free water. This water complies with the WFI quality (water for injection) of Pharmacopeia Europa. The liquid media are sterilized by filtration and bottled, the systems and methods of manufacture being such that entry of endotoxins and microbes is largely precluded.

The media that are preferred for use in the present invention show advantageous properties in relation to skin regeneration even if the media compositions are altered, such as, for example, with or without choline chloride, with or without $H_2SeO_3$.

The skin cell culture media and the mixture of biomolecules (collagen/chitosan/glycosylaminoglycan) and additives may advantageously be mixed into a cosmetic or dermatological preparation in a proportion of up to 99.9% by weight, based on the total weight of the preparation.

Some of the advantages associated with the preparation of the present invention which comprises a combination of certain components of cell culture media with the active ingredients collagen, chitosan and glycosylaminoglycan are illustrated in the Examples below.

In the present specification and the appended claims, cosmetic or dermatological preparations or matrices are intended to include topical preparations which are suitable for applying said media to the skin in fine distribution and preferably in a form which can be absorbed through the skin. Examples of application forms which are suitable for this purpose include aqueous and hydroalcoholic solutions, sprays, foams, foam aerosols, ointments, aqueous gels, emulsions of the O/W or W/O type, microemulsions, hydrophilic or lipophilic patches and cosmetic stick products. Particularly suitable carriers include aqueous gels, O/W emulsions, W/O/W emulsions and microemulsions. The preparation can also be used, for example, in body-cleansing compositions such as, e.g., soaps, shower baths, shampoos and the like.

Preferred cosmetic formulations include hydrogels and emulsions of any type, in particular O/W emulsions.

All lipids known for use in cosmetics can, for example, be employed as oily or lipid phase.

Preparations of the present invention in the form of an emulsion will usually comprise one or more emulsifiers. These emulsifiers may advantageously be chosen from non-ionic, anionic, cationic and amphoteric emulsifiers.

Besides water and physiologically suitable solvents, it is possible to use, inter alia, care constituents, oils, waxes, fats, refatting substances, thickeners, antioxidants, emulsifiers, substances suitable as sunscreen filters, enzymes, amino acids, proteins, polysaccharides and/or fragrances. According to the invention, apart from the aforementioned substances the preparations may optionally also comprise the additives that are customary in cosmetics, for example perfume, dyes, antimicrobial substances, refatting agents, complexing and sequestering agents, pearlescent agents, plant extracts, vitamins, active ingredients, preservatives, bactericides, coloring pigments, thickeners, emollients, moisturizers and/or humectants, and other usual ingredients of a cosmetic or dermatological formulation such as, e.g., alcohols, polyols, polymers, foam stabilizers, electrolytes, organic solvents and silicone derivatives.

Suitable preparations include also those which can be employed for professional wound management and wound healing and/or for the reduction of surgical scars and the like, such as, for example, polyurethane preparations in combination with chitosan/collagen/chondroitin 6-sulfate sponges or solutions.

Non-limiting examples of advantageous additives include specific active ingredients such as, for example, antioxidants. These antioxidants may advantageously be selected from amino acids (e.g. glycine, lysine, arginine, cysteine, cystine, histidine, tyrosine, tryptophan) and derivatives thereof (as salt, ester, ether, sugar, nucleotide, nucleoside, peptide and lipid compound), imidazoles (e.g., urocanic acid) and derivatives thereof (e.g., as salt, ester, ether, sugar, nucleotide, nucleoside, peptide and/or lipid compound), peptides such as D,L-carnosine, D-carnosine, L-carnosine, anserine and derivatives thereof (e.g., as salt, ester, ether, sugar, thiol, nucleotide, nucleoside, peptide and lipid compound), carotenoids, carotenes (e.g. α-carotene, β-carotene, ψ-lycopene, phytoene,) and derivatives thereof (e.g., as salt, ester, ether, sugar, nucleotide, nucleoside, peptide and/or lipid compound), chlorogenic acid and derivatives thereof (e.g., as salt, ester, ether, sugar, thiol, nucleotide, nucleoside, peptide and/or lipid compound), aurothioglucose, propylthiouracil and other thiols (e.g., thioredoxin, lipoic acid, glutathione, cysteine, cystine, cystamine and their glycosyl, N-acetyl, methyl, ethyl, propyl, amyl, butyl and lauryl, palmitoyl, oleyl, γ-linoleyl, cholesteryl and glyceryl esters) and the salts thereof, dilauryl thiodipropionate, distearyl thiodipropionate, thiodipropionic acid and derivatives thereof (e.g., as salt, ester, ether, sugar, thiol, nucleotide, nucleoside, peptide and/or lipid compound) and sulfoximine compounds (e.g., homocysteine sulfoximine, buthionine sulfones, penta-, hexa-, heptathionine sulfoximine) in very low tolerated dosages (e.g. pmol to μmol/kg). Also included are (metal) chelators (e.g., apoferritin, desferral, lactoferrin, α-hydroxy fatty acids, palmitic acid, phytic acid) and derivatives thereof (e.g., as salt, ester, ether, sugar, thiol, nucleotide, nucleoside, peptide and/or lipid compound), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g., γ-linolenic acid, linoleic acid, oleic acid), folic acid and derivatives thereof, furfurylidenesorbitol and derivatives thereof, ubiquinone, ubiquinol, plastoquinone and derivatives thereof (e.g., as salt, ester, ether, sugar, thiol, nucleotide, nucleoside, peptide and lipid compound), vitamin C and derivatives (e.g., ascorbyl palmitate, Mg ascorbyl phosphate, ascorbyl acetate), tocopherols and derivatives (e.g., vitamin E acetate), and phenolic compounds and plant extracts containing same such as, for example, flavonoids (e.g., glycosyl rutin, ferulic acid, caffeic acid), furfurylidene glucitol, butylated hydroxytoluene, butylated hydroxyanisole, nordihydroguaiaretic resin acid, nordihydroguaiaretic acid, trihydroxybutyrophenone and derivatives thereof (as salt, ester, ether, sugar, nucleotide, nucleoside, peptide and lipid compound), uric acid and derivatives thereof, mannose and derivatives thereof (e.g., as salt, ester, ether, sugar, thiol, nucleotide, nucleoside, peptide and lipid compound), zinc and its derivatives (e.g., ZnO, ZnSO$_4$), selenium and its derivatives (e.g., selenomethionine, ebselen), stilbenes and derivatives thereof (e.g., stilbene oxide, trans-stilbene oxide) and the derivatives (e.g., the salt, ester, ether, sugar, thiol, nucleotide, nucleoside, peptide and/or lipid compounds) of these active ingredients which are suitable according to the invention.

The additional use of a buffer may sometimes become necessary for stabilizing the ingredients of the disperse phase. In this regard, phosphate-buffered saline solutions and citrate buffers are examples of preferably employed buffers.

Besides antioxidants, combinations of the preparations of the present invention with specific ingredients which are preferably chosen from Q10, AGR, Zn orotate, carnitine, creatine and/or taurine are particularly preferred.

AGR (alpha-glucosyl rutin) belongs to the flavonoids which are found in most plants. AGR is capable of protecting the cells of the intrinsic immune system of the skin from environmental damage such as, e.g., from UV radiation.

Areas of application of the preparation of the present invention which have proved to be particularly advantageous include the care of all skin types with the exception of all septic inflammations, and also special applications such as microdermal abrasion, acid peeling and retinol treatments. The skin regeneration and soothing of the skin by the preparations of the present invention is evident in these cases.

An additional preferred field of application of the preparation of the present invention is cosmetic care of the skin, in particular for beautification.

The packaging for the preparation of the present invention can include all cosmetically customary dosage systems such as, e.g., jars, pump bottles, pipette bottles, cartridges or capsules.

For problematic formulations into which the cell medium cannot be incorporated, there is the possibility to mix the cell culture media and cosmetic product only shortly before use, through special packaging elements such as, for example, double cartridges with a mixing head as known, for example, from 2-component adhesives. The packaging of the cell culture medium may also be designed for refilling, so that only fresh product is used.

It also is advantageous to incorporate the matrix of the invention in a polyurethane matrix and configure the resultant product as cosmetic skin covering, wound covering in plasters or bandages or as pad. Non-limiting examples of polyurethane matrices which are suitable for these purposes include those which are described in DE 42 33 289, DE 43 08 347, DE 43 08 445, DE 43 28 190 and DE 101 28 685, the entire disclosures whereof are incorporated by reference herein.

DETAILED DESCRIPTION OF THE INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description making apparent to those skilled in the art how the several forms of the present invention may be embodied in practice.

Advantageous exemplary embodiments of the present invention follow. Unless indicated otherwise, the quantitative data are based on weight %. It is possible in all the preparations for the ratio of the matrix molecules collagen, chitosan and glycosylaminoglycan to be from about 0.00001% by weight to about 99% by weight of the final formulation, preferably from anbout 0.0005% by weight to about 50% by weight and ideally from about 0.0015% to about 30% by weight, based on the total weight of the preparation. The dispersant "culture medium" preferably corresponds to an osmotic pressure of an about 0.5% to about 2% sodium chloride solution, but ideally corresponds to the physiological osmotic pressure of human tissue, especially of the skin.

EXAMPLES

Example 1

Cream

| Formula (INCI/CTFA adopted names) | % w/w |
|---|---|
| WATER (AQUA) | 66.9268 |
| TRIISOSTEARIN | 4.0000 |
| BUTYLENE GLYCOL | 3.0209 |
| PETROLATUM | 2.7000 |
| GLYCERIN | 2.5800 |
| CETEARYL ETHYLHEXANOATE | 2.2500 |
| HYDROGENATED COCOGLYCERIDES | 2.0000 |
| CAPRYLIC/CAPRIC TRIGLYCERIDE | 2.0000 |
| CETEARYL ALCOHOL | 1.6000 |
| OLEA EUROPAEA (OLIVE) OIL UNSAPONIFIABLES | 1.5000 |
| PEG-30 STEARATE | 1.1000 |
| TOCOPHERYL ACETATE | 1.0000 |
| STEARIC ACID | 1.0000 |
| SORBETH-30 | 1.0000 |
| PALMITIC ACID | 1.0000 |
| CYCLOMETHICONE | 1.0000 |
| PHENOXYETHANOL | 0.7556 |
| STEARYL ALCOHOL | 0.5880 |
| POLOXAMER 188 | 0.5000 |
| BEESWAX (CERA ALBA) | 0.5000 |
| CETEARETH-20 | 0.4000 |
| SODIUM CARBOMER | 0.3300 |
| LANOLIN ALCOHOL | 0.3000 |
| CETYL ALCOHOL | 0.2640 |
| ISOPROPYL MYRISTATE | 0.2500 |
| GLYCERYL POLYMETHACRYLATE | 0.2150 |
| CETEARETH-25 | 0.2040 |
| METHYLPARABEN | 0.1526 |
| LECITHIN | 0.1490 |
| HISTIDINE | 0.1002 |
| SODIUM CITRATE | 0.1000 |
| DISODIUM EDTA | 0.1000 |
| CETEARETH-15 | 0.0900 |
| GLUCOSYLRUTIN | 0.0850 |
| BUTYLPARABEN | 0.0417 |
| ETHYLPARABEN | 0.0402 |
| MYRISTYL ALCOHOL | 0.0360 |
| ISOBUTYLPARABEN | 0.0204 |
| MYRETH-4 | 0.0180 |
| ASCORBYL PALMITATE | 0.0175 |
| SOLUBLE COLLAGEN | 0.0171 |
| ISOQUERCITRIN | 0.0150 |
| PROPYLPARABEN | 0.0110 |
| PROPYLENE GLYCOL | 0.0050 |
| CHITOSAN | 0.0046 |
| TOCOPHEROL | 0.0035 |
| SODIUM CHLORIDE | 0.0027 |
| SODIUM CHONDROITIN SULFATE | 0.0019 |
| GLUCOSE | 0.0019 |
| LYSINE HYDROCHLORIDE | 0.0006 |
| THREONINE | 0.0004 |
| ARGININE | 0.0004 |
| SERINE | 0.0002 |
| POTASSIUM CHLORIDE | 0.0002 |

-continued

| Formula (INCI/CTFA adopted names) | % w/w |
|---|---|
| TRYPTOPHAN | 0.0001 |
| MAGNESIUM SULFATE | 0.0001 |
| GLYCINE | 0.0001 |
| CALCIUM CHLORIDE | 0.0001 |
| FOLIC ACID | 0.0001 |
| CALCIUM PANTOTHENATE | 0.0001 |

The components HISTIDINE, GLUCOSE and CALCIUM CHLORIDE are the components of the aqueous phase which serves as the disperse phase.

Example 2

Cream

| Formula (INCI/CTFA adopted names) | % w/w |
|---|---|
| WATER (AQUA) | 71.1509 |
| GLYCERIN | 4.3000 |
| METHYLGLUCOSE SESQUISTEARATE | 3.2200 |
| TOCOPHERYL ACETATE | 2.0050 |
| PPG-15 STEARYL ETHER | 2.0000 |
| ETHYLHEXYL METHOXYCINNAMATE | 2.0000 |
| PANTHENOL | 1.8750 |
| TRIISOSTEARIN | 1.7000 |
| SORBITAN STEARATE | 1.3800 |
| ETHYLHEXYL PALMITATE | 1.3000 |
| ISOPROPYL STEARATE | 1.2000 |
| CAPRYLIC/CAPRIC TRIGLYCERIDE | 1.2000 |
| MACADAMIA TERNIFOLIA SEED OIL | 1.0000 |
| DIMETHICONE | 0.8000 |
| PHENOXYETHANOL | 0.7556 |
| MYRISTYL MYRISTATE | 0.6000 |
| OCTYLDODECANOL | 0.5470 |
| CYCLOMETHICONE | 0.5000 |
| GLYCERYL POLYMETHACRYLATE | 0.4300 |
| IRVINGIA GABONENSIS KERNEL BUTTER | 0.3100 |
| IMIDAZOLIDINYL UREA | 0.3000 |
| XANTHAN GUM | 0.1700 |
| TITANIUM DIOXIDE | 0.1550 |
| METHYLPARABEN | 0.1571 |
| HYDROGENATED COCO-GLYCERIDES | 0.1350 |
| DISODIUM EDTA | 0.1000 |
| BHT | 0.1000 |
| ACRYLATES/C10–30 ALKYL ACRYLATE CROSSPOLYMER | 0.1000 |
| RETINYL PALMITATE | 0.0990 |
| TROMETHAMINE | 0.0700 |
| CETEARYL ALCOHOL | 0.0500 |
| BUTYLPARABEN | 0.0447 |
| ETHYLPARABEN | 0.0402 |
| LECITHIN | 0.0350 |
| SODIUM PCA | 0.0250 |
| BUTYLENE GLYCOL | 0.0209 |
| ISOBUTYLPARABEN | 0.0204 |
| ALUMINA | 0.0200 |
| SOLUBLE COLLAGEN | 0.0171 |
| ASCORBYL PALMITATE | 0.0125 |
| PROPYLPARABEN | 0.0111 |
| PROPYLENE GLYCOL | 0.0100 |
| SILICA | 0.0088 |
| SODIUM POLYACRYLATE | 0.0075 |
| CHITOSAN | 0.0046 |
| TOCOPHEROL | 0.0035 |
| SODIUM CHLORIDE | 0.0027 |
| SODIUM CHONDROITIN SULFATE | 0.0019 |
| GLUCOSE | 0.0019 |
| LYSINE HYDROCHLORIDE | 0.0006 |
| THREONINE | 0.0004 |
| ARGININE | 0.0004 |
| SERINE | 0.0002 |
| POTASSIUM CHLORIDE | 0.0002 |

-continued

| Formula (INCI/CTFA adopted names) | % w/w |
|---|---|
| HISTIDINE | 0.0002 |
| TRYPTOPHAN | 0.0001 |
| MAGNESIUM SULFATE | 0.0001 |
| GLYCINE | 0.0001 |
| CALCIUM CHLORIDE | 0.0001 |
| FOLIC ACID | 0.0001 |
| CALCIUM PANTOTHENATE | 0.0001 |

Example 3

| Formula (INCI/CTFA adopted names) | % w/w |
|---|---|
| WATER (AQUA) | 91.8039 |
| GLYCERIN | 2.5800 |
| SD ALCOHOL 39-C (ALCOHOL DENAT.) | 2.0000 |
| PANTHENOL | 1.1250 |
| PROPYLENE GLYCOL | 0.5000 |
| GLYCERYL POLYMETHACRYLATE | 0.5000 |
| SODIUM CARBOMER | 0.4400 |
| XANTHAN GUM | 0.3000 |
| IMIDAZOLIDINYL UREA | 0.3000 |
| METHYLPARABEN | 0.1521 |
| TRISODIUM EDTA | 0.1400 |
| CITRIC ACID | 0.0500 |
| BIOTIN | 0.0400 |
| BUTYLENE GLYCOL | 0.0209 |
| SOLUBLE COLLAGEN | 0.0171 |
| PHENOXYETHANOL | 0.0156 |
| CHITOSAN | 0.0046 |
| SODIUM CHLORIDE | 0.0027 |
| SODIUM CHONDROITIN SULFATE | 0.0019 |
| GLUCOSE | 0.0019 |
| BUTYLPARABEN | 0.0017 |
| LYSINE HYDROCHLORIDE | 0.0006 |
| THREONINE | 0.0004 |
| ARGININE | 0.0004 |
| SERINE | 0.0002 |
| POTASSIUM CHLORIDE | 0.0002 |
| HISTIDINE | 0.0002 |
| TRYPTOPHAN | 0.0001 |
| MAGNESIUM SULFATE | 0.0001 |
| GLYCINE | 0.0001 |
| CALCIUM CHLORIDE | 0.0001 |
| FOLIC ACID | 0.0001 |
| CALCIUM PANTOTHENATE | 0.0001 |

Example 4

| Formula (INCI/CTFA adopted names) | % w/w |
|---|---|
| WATER (AQUA) | 50.5510 |
| OCTOCRYLENE | 10.0000 |
| GLYCERIN | 7.5000 |
| CETEARYL ALCOHOL | 3.1000 |
| C12–15 ALKYL BENZOATE | 3.0000 |
| TITANIUM DIOXIDE | 2.4000 |
| TOCOPHERYL ACETATE | 2.0000 |
| DIETHYLHEXYL BUTAMIDO TRIAZONE | 2.0000 |
| CETEARETH-20 | 2.0000 |
| BIS-ETHYLHEXYLOXYPHENOL METHOXYPHENOL TRIAZINE | 2.0000 |
| HYDROGENATED COCO-GLYCERIDES | 1.0000 |
| GLYCERYL STEARATE | 0.7000 |
| PROPYLENE GLYCOL | 0.6250 |
| PEG-40 CASTOR OIL | 0.6000 |
| PHENOXYETHANOL | 0.5180 |

-continued

| Formula (INCI/CTFA adopted names) | % w/w |
|---|---|
| FUMARIA OFFICINALIS (FUMITORY) EXTRACT | 0.5000 |
| CITRUS MEDICA LIMONUM (LEMON) EXTRACT | 0.5000 |
| MICA | 0.3240 |
| SODIUM CETEARYL SULFATE | 0.3000 |
| FRAGRANCE (PERFUME) | 0.3000 |
| DMDM HYDANTOIN | 0.2850 |
| XANTHAN GUM | 0.2000 |
| TRISODIUM EDTA | 0.1990 |
| FUMARIC ACID | 0.1250 |
| METHYLPARABEN | 0.1050 |
| TRIMETHOXYCAPRYLYLSILANE | 0.1000 |
| ETHYLPARABEN | 0.0280 |
| BUTYLPARABEN | 0.0280 |
| IODOPROPYNYL BUTYLCARBAMATE | 0.0150 |
| ISOBUTYLPARABEN | 0.0140 |
| PROPYLPARABEN | 0.0070 |
| IRON OXIDES | 0.4200 |
| TITANIUM DIOXIDE | 0.2400 |
| IRON OXIDES | 0.1960 |
| ULTRAMARINES | 0.0800 |
| IRON OXIDES | 0.0400 |
| COLLAGEN | 0.03 |
| CHITOSAN | 0.01 |
| CHONDROITIN SULFATE | 0.005 |
| ARGININE | 0.0004 |
| SERINE | 0.0002 |
| POTASSIUM CHLORIDE | 0.0002 |
| HISTIDINE | 0.0002 |
| TRYPTOPHAN | 0.0001 |
| MAGNESIUM SULFATE | 0.0001 |
| GLYCINE | 0.0001 |
| CALCIUM CHLORIDE | 0.0001 |
| FOLIC ACID | 0.0001 |

Example 5

O/W Emulsion

| | |
|---|---|
| KERATINOCYTE MEDIUM MCDB153 | 40% by weight |
| COLLAGEN/CHITOSAN/CHONDROITIN SULFATE matrix plus, blended in any proportion: | 6% by weight |
| WATER (AQUA) | |
| GLYCERIN | |
| HYDROGENATED COCO-GLYCERIDES | |
| SQUALANE | |
| GLYCERYL STEARATE CITRATE | |
| CAPRYLIC/CAPRIC TRIGLYCERIDE | |
| ETHYLHEXYL COCOATE | |
| MYRISTYL ALCOHOL | |
| BUTYROSPERMUM PARKII (SHEA BUTTER) | |
| BUTYLENE GLYCOL | |
| CETYL ALCOHOL | |
| TOCOPHERYL ACETATE | |
| PHENOXYETHANOL | |
| SODIUM CHLORIDE | |
| IMIDAZOLIDINYL UREA | |
| CARBOMER | |
| XANTHAN GUM | |
| METHYLPARABEN | |
| EDTA | |
| SODIUM HYDROXIDE | |
| BHT | |
| ETHYLPARABEN | |
| BUTYLPARABEN | |
| ISOBUTYLPARABEN | |
| PROPYLPARABEN | |

Example 6

W/O/W Emulsion

| | % by weight |
|---|---|
| PEG-100 stearate | 2.00% |
| Glyceryl stearate | 4.00% |
| Squalane | 1.50% |
| Squalene | 1.50% |
| Isopropyl palmitate | 5.40% |
| MCDB 153/DME 1:1 | 0.360% |
| Magnesium sulfate | 0.240% |
| Preservative | 0.50% |
| COLLAGEN/CHONDROITIN SULFATE/CHITOSAN | 5% |
| Water VES | ad 100.00 |

The fatty phase containing the emulsifier is heated to 80° C. The aqueous phase without the part that contains the medium is heated to 80° C. as well. The two phases are combined at 80° C., homogenized for about 3-10 minutes and then cooled to 48° C. or room temperature. Then, keeping the temperature constant to ±1° C., the part of the aqueous phase which contains the medium is added and mixed.

Example 7

| | |
|---|---|
| PEG-40 stearate | 1.00% |
| Glyceryl stearate | 2.00% |
| Cetyl alcohol | 3.00% |
| Mineral oil DAB 9 | 2.00% |
| Safflower oil | 2.00% |
| Isopropyl palmitate | 4.50% |
| Glycerin | 3.00% |
| Magnesium sulfate | 1.20% |
| Preservative | 0.50% |
| Collagen/chitosan/glycosylaminoglycan matrix | 2.00% |
| Deionized water | ad 100.00% |
| of which DMEM/HAM F12 (1:1) | 2.5% |

Example 8

| | |
|---|---|
| PEG-80 stearate | 2.00% |
| Cetyl alcohol | 3.00% |
| Mineral oil DAB 9 | 1.50% |
| Evening primrose oil | 2.50% |
| Isopropyl palmitate | 5.40% |
| Propylene glycol | 3.00% |
| Potassium chloride | 0.60% |
| Preservative | 0.50% |
| Collagen/chitosan/glycosylaminoglycan matrix | 1.50% |
| Water VES | ad 100.00% |
| of which DMEM/HAM F12 (1:1) | 5% |

Example 9

| | |
|---|---|
| Steareth-100 | 2.00% |
| Myristyl alcohol | 1.00% |
| Mineral oil DAB 9 | 3.00% |

-continued

| | |
|---|---|
| Castor oil | 3.00% |
| Cyclomethicone | 2.00% |
| Propylene glycol | 3.00% |
| Glycerin | 5.00% |
| Potassium chloride | 3.00% |
| Collagen/chitosan/glycosylaminoglycan matrix | 4.50% |
| Preservative | 0.50% |
| Water VES | ad 100.00% |
| of which MCDB 153 | 0.5% |

Example 10

| | |
|---|---|
| Steareth-20 | 2.00% |
| Cetearyl | 3.00% |
| Petrolatum | 0.50% |
| Wheat germ oil | 1.50% |
| Dimethicone | 5.00% |
| Glycerin | 5.00% |
| Sodium chloride | 3.00% |
| Preservative | 0.50% |
| PUR | 1.50% |
| Collagen/chitosan/glycosylaminoglycan matrix | 5.65% |
| Water VES | ad 100.00% |
| of which DMEM/HAM F12 (1:1) | 15% |

Example 11

| | |
|---|---|
| Dimethicone copolyol | 2.00% |
| Cetearyl alcohol | 3.00% |
| Petrolatum | 0.50% |
| Wheat germ oil | 1.50% |
| Dimethicone | 5.00% |
| Glycerin | 5.00% |
| Sodium chloride | 3.00% |
| Preservative | 0.50% |
| Collagen/chitosan/glycosylaminoglycan matrix | 6.05% |
| Water VES | ad 100.00% |
| of which MCDB 153 | 1.5% |

Example 12

| | |
|---|---|
| PEG-20 behenate | 2.00% |
| Stearyl alcohol | 3.00% |
| Petrolatum | 1.00% |
| Grape seed oil | 3.00% |
| Dimethicone | 3.00% |
| Sorbitol | 5.00% |
| Zinc sulfate | 3.00% |
| Preservative | 0.50% |
| Collagen/chitosan/glycosylaminoglycan matrix | 10.5% |
| Water VES | ad 100.00% |
| of which MCDB 153 | 5% |

Example 13

| | |
|---|---|
| Decaglyn 1-IS | 2.00% |
| Stearyl alcohol | 3.00% |
| Petrolatum | 1.00% |
| Grape seed oil | 3.00% |
| Dimethicone | 3.00% |
| Sorbitol | 5.00% |
| Zinc sulfate | 3.00% |
| Preservative | 0.50% |
| Collagen/chitosan/glycosylaminoglycan matrix | 25.00% |
| Water VES | ad 100.00% |
| of which MCDB 153 | 40% |

Example 14

| | |
|---|---|
| PEG-20 myristate | 2.00% |
| Stearyl alcohol | 3.00% |
| Petrolatum | 2.00% |
| Castor oil | 5.00% |
| Dimethicone | 5.00% |
| Sorbitol | 5.00% |
| Zinc sulfate | 3.00% |
| Preservative | 0.50% |
| Collagen/chitosan/glycosylaminoglycan matrix | 3.5% |
| Water VES | ad 100.00% |
| of which MCDB 153/RPMI 1640/serum substitutes | 0.1% |

Example 15

| | |
|---|---|
| Sucrose laurate | 2.00% |
| Stearyl alcohol | 3.00% |
| Petrolatum | 2.00% |
| Castor oil | 5.00% |
| Dimethicone | 5.00% |
| Sorbitol | 5.00% |
| Zinc sulfate | 3.00% |
| Preservative | 0.50% |
| Collagen/chitosan/glycosylaminoglycan matrix | 8.50% |
| Water VES | ad 100.00% |
| of which MCDB 153 | 12% |

Example 16

| | |
|---|---|
| PEG-80 behenate | 2.00% |
| Glyceryl behenate | 4.00% |
| Squalane | 3.00% |
| Castor oil | 5.40% |
| Glycerin | 6.00% |
| Magnesium sulfate | 2.60% |
| Preservative | 0.50% |
| Collagen/chitosan/glycosylaminoglycan matrix | 0.0655 |
| Water VES | ad 100.00% |
| of which MCDB 153/DME | 8.5% |

Example 17

O/W Emulsion

| | |
|---|---|
| Glyceryl stearate citrate | 3.00% |
| Stearyl alcohol | 1.00% |
| Octyldodecanol | 1.00% |
| Caprylic/capric triglyceride | 1.00% |
| Dicaprylyl ether | 1.00% |
| Carbomer | 0.15% |
| Glycerin | 3.00% |
| Perfume, preservative, NaOH dyes, antioxidants, etc. | q.s. |
| Collagen/chitosan/glycosylaminoglycan matrix | 4.0% |
| Water | ad 100.00% |
| of which DMEM/HAM's F-12 (1:1) | 2.5% |
| pH adjusted to | 5.5 |

Example 18

O/W Emulsion

| | |
|---|---|
| Glyceryl stearate citrate | 3.00% |
| Stearyl alcohol | 1.00% |
| Octyldodecanol | 0.25% |
| Caprylic/capric triglyceride | 0.25% |
| Dicaprylyl ether | 0.25% |
| Carbomer | 0.15% |
| Glycerin | 3.00% |
| Perfume, preservative, NaOH dyes, antioxidants, etc. | q.s. |
| Collagen/chitosan/glycosylaminoglycan matrix | 5.0% |
| Water | ad 100.00% |
| of which MCDB 153 | 0.5% |
| pH adjusted to | 5.5 |

Example 19

O/W Emulsion

| | |
|---|---|
| Glyceryl stearate citrate | 3.00% |
| Behenyl alcohol | 1.00% |
| Dimethicone | 1.50% |
| Cycolmethicone | 1.50% |
| Carbomer | 0.15% |
| Glycerin | 6.00% |
| Perfume, preservative, NaOH dyes, antioxidants, etc. | q.s. |
| Collagen/chitosan/glycosylaminoglycan matrix | 7.5% |
| Water | ad 100.00 |
| of which DMEM/HAM's F-12 (1:1) | 5% |
| pH adjusted to | 5.5 |

Example 20

O/W Emulsion

| | |
|---|---|
| Glyceryl stearate citrate | 3.00% |
| Stearyl alcohol | 1.00% |
| Octyldodecanol | 0.25% |
| Caprylic/capric triglyceride | 0.25% |
| Dicaprylyl ether | 0.25% |
| Dimethicone | 0.50% |
| Carbomer | 0.15% |
| Glycerin | 3.00% |
| Aluminum starch octenyl succinate | 0.50% |
| Talc | 0.50% |
| Bentonite | 0.10% |
| Collagen/chitosan/glycosylaminoglycan matrix | 0.40% |
| Perfume, preservative, NaOH dyes, antioxidants etc. | q.s. |
| Water | ad 100.00 |
| of which MCDB 153 | 80% |
| pH adjusted to | 5.5 |

Example 21

O/W Emulsion

| | |
|---|---|
| Glyceryl stearate citrate | 3.00% |
| Cetyl alcohol | 1.00% |
| Squalane | 1.00% |
| Jojoba oil | 1.00% |
| Liquid paraffin | 1.00% |
| Carbomer | 0.10% |
| Glycerin | 3.00% |
| Serine | 0.50% |
| Tocopherol acetate | 1.00% |
| Carbomer | 0.10% |
| Xanthan gum | 0.10% |
| Collagen/chitosan/glycosylaminoglycan matrix | 1.0% |
| Perfume, preservative, NaOH dyes, antioxidants etc. | q.s. |
| Water | ad 100.00 |
| of which MCDB 153 | 75.5% |
| pH adjusted to | 6.0 |

Example 22

O/W Emulsion

| | |
|---|---|
| Glyceryl stearate citrate | 3.00% |
| Cetyl alcohol | 0.50% |
| Octyldodecanol | 0.40% |
| Caprylic/capric triglyceride | 0.40% |
| Dicaprylyl ether | 0.40% |
| Carbomer | 0.10% |
| Glycerin | 3.00% |
| Serine | 0.50% |
| Collagen/chitosan/glycosylaminoglycan matrix | 1.2% |
| Perfume, preservative, NaOH dyes, antioxidants etc. | q.s. |
| Water | ad 100.00 |
| of which MCDB 153 | 45.5% |
| pH adjusted to | 5.5 |

Example 23

Emulsion Make Up

| | |
|---|---|
| Glyceryl stearate citrate | 3.00% |
| Stearyl alcohol | 1.00% |
| Dimethicone | 0.50% |
| Glycerin | 1.50% |
| 1,3 Butylene glycol | 1.50% |
| Magnesium silicate | 1.00% |
| Mica | 1.00% |
| Iron oxides | 1.00% |
| Titanium dioxide | 2.50% |
| Talc | 5.00% |
| Carbomer | 0.15% |
| Collagen/chitosan/glycosylaminoglycan matrix | 0.50% |
| Perfume, preservative, NaOH, dyes, antioxidants etc. | q.s. |
| Water | ad 100.00 |
| of which MCDB 153/Ham's F12/RPMI 1640 | 0.5% |
| pH adjusted to | 5.5 |

Example 24

O/W Emulsion

| | |
|---|---|
| Glyceryl stearate citrate | 3.00% |
| Stearyl alcohol | 1.00% |
| Octyldodecanol | 0.25% |
| Caprylic/capric triglyceride | 0.25% |
| Dicaprylyl ether | 0.25% |
| Octyl methoxycinnamate | 4.00% |
| Benzophenone-3 | 3.00% |
| Octyl salicylate | 3.00% |
| Carbomer | 0.15% |
| Glycerin | 3.00% |
| Collagen/chitosan/glycosylaminoglycan matrix | 1.75% |
| Perfume, preservative, NaOH dyes, antioxidants etc. | q.s. |
| Water | ad 100.00 |
| of which MCDB 153 | 40% |
| pH adjusted to | 5.5 |

Example 25

O/W Emulsion

| | |
|---|---|
| Glyceryl stearate citrate | 3.00% |
| Stearyl alcohol | 1.00% |
| Octyldodecanol | 0.50% |
| Caprylic/capric triglyceride | 0.50% |
| Dicaprylyl ether | 0.50% |
| Distarch phosphate | 1.00% |
| Ethanol | 10.00% |
| Carbomer | 0.15% |
| Glycerin | 3.00% |
| Collagen/chitosan/glycosylaminoglycan matrix | 0.0625% |
| Perfume, preservative, NaOH, dyes, antioxidants etc. | q.s. |
| Water | ad 100.00 |
| of which MCDB 153 | 35% |
| pH adjusted to | 5.5 |

Example 26

Emulsifier Gel

| | |
|---|---|
| Glyceryl stearate citrate | 3.00% |
| Stearyl alcohol | 1.00% |
| Ethanol | 2.00% |
| Aluminum starch octenyl succinate | 0.25% |
| Talc | 0.25% |
| Tapioca starch | 0.25% |
| Carbomer | 0.15% |
| Glycerin | 3.00% |
| Collagen/chitosan/glycosylaminoglycan matrix | 0.10% |
| Perfume, preservative, NaOH dyes, antioxidants etc. | q.s. |
| Water | ad 100.00 |
| of which DMEM/HAM's F-12 (1:1) | 3.5% |
| pH adjusted to | 5.5 |

Example 27

Testing

To investigate the effect of the substances (d) used in the preparation of the present invention on the viability of human normal fibroblasts the following testing was carried out.

A test sample according to the present invention of the following composition was prepared, filtered through a 0.22 µm filter and diluted in a Fetal Calf Serum (FCS) depleted cell culture media F2 (DMEM/HAM F12 (1:1) containing 2% of FCS and antibiotics) at concentrations of 1%, 2%, 3% and 5% (w/w).

| Components (INCI/CTFA adopted names) | % w/w |
|---|---|
| Water (Aqua) | 98.2691 |
| Butylene Glycol | 0.5 |
| Soluble Collagen | 0.41 |
| Phenoxyethanol | 0.375 |
| Chitosan | 0.11 |
| Sodium Chloride | 0.064 |
| Methylparaben | 0.05 |
| Sodium Chondroitin Sulfate | 0.046 |
| Glucose | 0.045 |
| Butylparaben | 0.04 |
| Propylparaben | 0.02 |
| Lysine Hydrochloride | 0.0146 |
| Isobutylparaben | 0.01 |
| Threonine | 0.0095 |
| Arginine | 0.0084 |
| Ethylparaben | 0.005 |
| Histidine | 0.0042 |
| Serine | 0.0042 |
| Potassium Chloride | 0.004 |
| Glycine | 0.003 |
| Calcium Chloride | 0.0026 |
| Magnesium Sulfate | 0.002 |
| Tryptophan | 0.0016 |
| Sodium Phosphate | 0.0014 |
| Folic Acid | 0.0004 |
| Calcium Panthothenate | 0.00004 |

In parallel a comparative test sample which consisted only of water, collagen, chitosan and sodium chondroitin sulfate in the same relative weight ratios as in the test sample according to the invention was prepared and diluted with F12 media to concentrations of 1%, 2%, 3% and 5% (w/w).

Incubation Protocol

Human Normal Fibroplasts (P8) were cultured in F12 media and placed in a 24 well culture plate at a cell density of 20,000 cells/well in 100 μL of F2 media per well. In a controlled atmosphere the cells were incubated with 900 μL of test composition per well at 37° C. for 24 hours and 48 hours. Pure F2 media was used as negative control (NC) and media which differs from F2 media by containing 10% instead of 2% of FCS was used as positive control (PC). All experiments wered conducted in tetraplicate (n=4).

Evaluation Protocol

The viability of the cells after the 24 and 48 hour incubation periods was evaluated by measuring their alkaline phosphatase activity. Specifically, the p-nitrophenyl phosphate (PNPP) reduction capacity of the incubated cells at pH 5 during 45 minutes was followed spectroscopically at a wavelength of 405 nm.

Statistics

Data from the assays were expressed as mean+/−Standard Deviation (S.D.). The statistical significance between the groups was assessed by the student t test.

Results

The following table lists the obtained results in terms % activation of the cells incubated with the various tested samples compared to cells that were incubated with the negative control (NC).

TABLE

Cell Proliferation Results

| Tested Sample | Raw Data (mean) | Raw Data (S.D.) | % Activation vs. NC |
|---|---|---|---|
| NC | 0.021 | 0.022 | 100 |
| PC | 0.023 | 0.020 | 110 |
| Invention 1% | 0.034 | 0.009 | 162 |
| Invention 2% | 0.048 | 0.003 | 229 |
| Invention 3% | 0.052 | 0.005 | 248* |
| Invention 5% | 0.062 | 0.005 | 295* |
| Comparative 1% | 0.026 | 0.015 | 124 |
| Comparative 2% | 0.030 | 0.005 | 143 |
| Comparative 3% | 0.009 | 0.006 | 43 |
| Comparative 5% | 0.027 | 0.022 | 129 |

*significantly different from Negative Control (NC) group ($p < 0.01$)

The data summarized in the above table shows that the substances of group (d) in combination with a collagen/chitosan/glycosylaminoglycan combination induce cell proliferation in a dose-related way. Cell proliferation was strongly and significantly improved when the test sample according to the invention was used at concentrations of 3% and 5% (w/w), with values of +248% and +295% versus the negative control, respectively.

In comparison, the collagen/chitosan/glycosylaminoglycan combination alone (i.e., without the substances of group (d)) did not appear to be capable of significantly inducing cell proliferation, and even seemed to exhibit cytotoxicity when used at high concentrations.

It is noted that the foregoing examples have been provided merely for the purpose of explanation and are in no way to be construed as limiting of the present invention. While the present invention has been described with reference to an exemplary embodiment, it is understood that the words that have been used are words of description and illustration, rather than words of limitation. Changes may be made, within the purview of the appended claims, as presently stated and as amended, without departing from the scope and spirit of the present invention in its aspects. Although the invention has been described herein with reference to particular means, materials and embodiments, the invention is not intended to be limited to the particulars disclosed herein. Instead, the invention extends to all functionally equivalent structures, methods and uses, such as are within the scope of the appended claims.

What is claimed is:

1. A cosmetic or dermatological preparation, wherein the preparation is ready for application to skin, is in the form of at least one of a gel, an O/W emulsion, a W/O/W emulsion, a W/O emulsion, a microemulsion, an ointment, a cream, a dusting powder, a foam, an aerosol preparation, and a cosmetic stick, and is obtainable by combining substances comprising
   (a) at least one of collagen and a derivative thereof;
   (b) at least one of chitosan and an acetyl derivative thereof with a degree of acetylation of up to about 50%;
   (c) at least one of a glycosylaminoglycan and a derivative thereof; and
   (d) at least ten substances selected from amino acids, α-biotin, $(NH_4)_6Mo_7O_{24}$, adenine, $AlCl_3$, biotin, $CaCl_2$, calcium pantothenate, choline chloride, $CoCl_2$, $CrK(SO_4)_2$, $CuSO_4$, D-Ca pantothenate, $EDTA.Na_2$, $EDTA.Na_3$, $Fe(NO_3)_3$, $FeSO_4$, folic acid, glucose, $H_2SeO_3$, HEPES, hypoxanthine, insulin human, KCl, linoleic acid, lipoic acid, $MgCl_2$, $MnCl_2$, $MnSO_4$, myoinositol, $Na_2HPO_4$, $Na_2SeO_3$, $Na_2SiO_3$, NaCl, $NaH_2PO_4$, $NaHCO_3$, sodium pyruvate, sodium acetate, $NH_4VO_3$, $NiCl_2$, nicotinamide, phenol red, polysorbate 80, putrescine, putrescine 2HCl, pyridoxine HCl, pyridoxal HCl, riboflavin, $SnCl_2$, thiamine HCl, thymidine, vitamin $B_{12}$, and $ZnSO_4$, substances (a) to (c) being employed in a total amount of from about 0.0005% to about 50% by weight, based on a total weight of the preparation.

2. The preparation of claim 1, wherein the amino acids comprise one or more of L-alanine, L-arginine, L-asparagine, L-aspartic acid, L-cysteine, L-cystine, glycine, L-glutamine, L-glutamic acid, L-histidine, L-isoleucine, L-leucine, L-lysine, L-methionine, L-phenylalanine, L-proline, L-serine, L-threonine, L-tryptophan, L-tyrosine, L-valine, and the hydrochloride salts thereof.

3. The preparation of claim 1, wherein at least fifty substances from group (d) are employed.

4. The preparation of claim 1, wherein one or more of glucose, folic acid, L-lysine, L-threonine, L-arginine, L-serine, L-histidine, and L-glycine are employed.

5. The preparation of claim 4, wherein at least three of glucose, folic acid, L-lysine, L-threonine, L-arginine, L-serine, L-histidine, and glycine are employed.

6. The preparation of claim 5, wherein at least five of glucose, folic acid, L-lysine, L-threonine, L-arginine, L-serine, L-histidine, and glycine are employed.

7. The preparation of claim 1, wherein glucose, folic acid, L-lysine, L-threonine, L-arginine, L-serine, L-histidine, and glycine are employed.

8. The preparation of claim 1, wherein at least one of substances (a) and (b) is of marine origin or of synthetic origin.

9. The preparation of claim 1, wherein the collagen comprises one or more collagens selected from types 1, 3, 4 and 5.

10. The preparation of claim 1, wherein the chitosan comprises chitosan having a molecular weight of from about 80,000 g/mol to about 15,000,000 g/mol.

11. The preparation of claim 10, wherein the chitosan comprises chitosan obtained from at least one of crustaceans and insects.

12. The preparation of claim 1, wherein the glycosylaminoglycan comprises at least one of chondroitin 4-sulfate and chondroitin 6-sulfate.

13. The preparation of claim 1, wherein substances (a) to (c) are employed in a total amount of from about 0.0015% to about 30% by weight.

14. The preparation of claim 1, wherein substances (a) to (c) are employed in a total amount of from about 0.005% to about 10% by weight.

15. The preparation of claim 1, wherein substances (a) to (c) are employed in a total amount of from about 0.01% to about 1% by weight, based on a total weight of the preparation.

16. The preparation of claim 1, wherein substances (a) to (c) are employed in a total amount of from about 0.015% to about 0.1% by weight.

17. The preparation of claim 1, wherein a weight ratio of substances (a) and (c) is from about 35:1 to about 3:1.

18. The preparation of claim 13, wherein a weight ratio of substances (a) and (c) is from about 20:1 to about 6:1.

19. The preparation of claim 14, wherein a weight ratio of substances (a) and (c) is from about 10:1 to about 8:1.

20. The preparation of claim 1, wherein a weight ratio of substances (a) and (b) is from about 10:1 to about 1.5:1.

21. The preparation of claim 13, wherein a weight ratio of substances (a) and (b) is from about 7:1 to about 2.5:1.

22. The preparation of claim 14, wherein a weight ratio of substances (a) and (b) is from about 5:1 to about 3.5:1.

23. The preparation of claim 1, wherein a weight ratio of substances (b) and (c) is from about 10:1 to about 1:1.

24. The preparation of claim 13, wherein a weight ratio of substances (b) and (c) is from about 5:1 to about 1.5:1.

25. The preparation of claim 14, wherein a weight ratio of substances (b) and (c) is from about 3:1 to about 2:1.

26. The preparation of claim 1, wherein the preparation comprises one or more skin cell culture media.

27. The preparation of claim 26, wherein the skin cell culture media comprise at least one of DMEM/HAM F12 (1:1) and MCDB 153.

28. The preparation of claim 26, wherein the skin cell culture media are selected from one or more of physiological saline solution, nutrient media, and complete media for culturing primary body cells.

29. The preparation of claim 26, wherein the one or more skin cell culture media comprise culture media for at least one of primary fibroblasts and keratinocytes.

30. The preparation of claim 28, wherein the complete media are supplemented with serum substitutes.

31. The preparation of claim 1, wherein the preparation further comprises a citrate buffer.

32. The preparation of claim 1, wherein the preparation further comprises at least one of Q10, alpha-glucosyl rutin, an alpha-hydroxy acid, Zn orotate, carnitine, creatine, and taurine.

33. The preparation of claim 1, wherein the preparation comprises water.

34. The preparation of claim 33, wherein the preparation comprises at least about 30% by weight of water, based on a total weight of the preparation.

35. The preparation of claim 33, wherein the preparation comprises at least about 50% by weight of water, based on a total weight of the preparation.

36. The preparation of claim 26, wherein the preparation comprises at least about 50% by weight of water, based on a total weight of the preparation.

37. The preparation of claim 1, wherein the preparation is present as an aqueous gel.

38. The preparation of claim 1, wherein the preparation is present as an O/W emulsion.

39. The preparation of claim 1, wherein the preparation is present as a W/O emulsion.

40. The preparation of claim 1, wherein the preparation is present as a microemulsion.

41. The preparation of claim 1, wherein the preparation is present as a cosmetic stick.

42. The preparation of claim 1, wherein the preparation is present as an ointment.

43. The preparation of claim 1, wherein the preparation is present as a cream.

44. The preparation of claim 1, wherein the preparation is present as a dusting powder.

45. The preparation of claim 1, wherein the preparation is present as a foam.

46. The preparation of claim 1, wherein the preparation is present as an aerosol preparation.

47. A cosmetic or dermatological preparation, wherein the preparation is ready for application to skin, is in the form of at least one of a gel, an O/W emulsion, a W/O/W emulsion, a W/O emulsion, a microemulsion, an ointment, a cream, a dusting powder, a foam, an aerosol preparation, and a cosmetic stick, and is obtainable by combining substances comprising
  (a) at least one of collagen and a derivative thereof, the collagen comprising one or more collagens selected from types 1, 3, 4 and 5;
  (b) at least one of chitosan and an acetyl derivative thereof with a degree of acetylation of up to about 50%, the chitosan comprising chitosan having a molecular weight of from about 80,000 g/mol to about 15,000,000 g/mol;
  (c) at least one of a glycosylaminoglycan and a derivative thereof, the glycosylaminoglycan comprising at least one of chondroitin 4-sulfate and chondroitin 6-sulfate; and
  (d) at least ten substances selected from amino acids, α-biotin, $(NH_4)_6Mo_7O_{24}$, adenine, $AlCl_3$, biotin, $CaCl_2$, calcium pantothenate, choline chloride, $CoCl_2$, $CrK(SO_4)_2$, $CuSO_4$, D-Ca pantothenate, $EDTA.Na_2$, $EDTA.Na_3$, $Fe(NO_3)_3$, $FeSO_4$, folic acid, glucose, $H_2SeO_3$, HEPES, hypoxanthine, insulin human, KCl, linoleic acid, lipoic acid, $MgCl_2$, $MnCl_2$, $MnSO_4$, myo-inositol, $Na_2HPO_4$, $Na_2SeO_3$, $Na_2SiO_3$, NaCl, $NaH_2PO_4$, $NaHCO_3$, sodium pyruvate, sodium acetate, $NH_4VO_3$, $NiCl_2$, nicotinamide, phenol red, polysorbate 80, putrescine, putrescine 2HCl, pyridoxine HCl, pyridoxal HCl, riboflavin, $SnCl_2$, thiamine HCl, thymidine, vitamin $B_{12}$, and $ZnSO_4$,
substances (a) to (c) being employed in a total amount of from about 0.005% to about 10% by weight, based on a total weight of the preparation.

48. The preparation of claim 47, wherein at least three of glucose, folic acid, L-lysine, L-threonine, L-arginine, L-serine, L-histidine, and glycine are employed.

49. The preparation of claim 47, wherein substances (a) to (c) are employed in a total amount of from about 0.01% to about 1% by weight, based on a total weight of the preparation.

50. The preparation of claim 47, wherein a weight ratio of substances (a) and (c) is from about 10:1 to about 8:1.

51. The preparation of claim 47, wherein a weight ratio of substances (a) and (b) is from about 7:1 to about 2.5:1.

52. The preparation of claim 49, wherein a weight ratio of substances (a) and (b) is from about 5:1 to about 3.5:1.

53. The preparation of claim 47, wherein a weight ratio of substances (b) and (c) is from about 10:1 to about 1:1.

54. The preparation of claim 49, wherein a weight ratio of substances (b) and (c) is from about 5:1 to about 1.5:1.

55. The preparation of claim 50, wherein a weight ratio of substances (b) and (c) is from about 3:1 to about 2:1.

56. The preparation of claim 47, wherein the preparation comprises one or more skin cell culture media.

57. The preparation of claim 56, wherein the skin cell culture media comprise at least one of DMEM/HAM F12 (1:1) and MCDB 153.

58. The preparation of claim 56, wherein the one or more skin cell culture media comprise culture media for at least one of primary fibroblasts and keratinocytes.

59. The preparation of claim 47, wherein the preparation further comprises a citrate buffer.

60. The preparation of claim 47, wherein the preparation further comprises at least one of Q10, alpha-glucosyl rutin, an alpha-hydroxy acid, Zn orotate, carnitine, creatine and taurine.

61. The preparation of claim 47, wherein the preparation comprises at least about 30% by weight of water, based on a total weight of the preparation.

62. The preparation of claim 47, wherein the preparation comprises at least about 50% by weight of water, based on a total weight of the preparation.

63. The preparation of claim 47, wherein the preparation is present as an aqueous gel.

64. The preparation of claim 47, wherein the preparation is present as an O/W emulsion.

65. The preparation of claim 47, wherein the preparation is present as a W/O emulsion.

66. A cosmetic or dermatological preparation, wherein the preparation is ready for application to skin, is in the form of at least one of a gel, an O/W emulsion, a W/O/W emulsion, a W/O emulsion, a microemulsion, an ointment, a cream, a dusting powder, a foam, an aerosol preparation, and a cosmetic stick, and is obtainable by combining substances comprising
(a) at least one of collagen and a derivative thereof, the collagen comprising one or more collagens selected from types 1, 3, 4 and 5;
(b) at least one of chitosan and an acetyl derivative thereof with a degree of acetylation of up to about 50%, the chitosan comprising chitosan having a molecular weight of from about 80,000 g/mol to about 15,000,000 g/mol;
(c) at least one of a glycosylaminoglycan and a derivative thereof, the glycosylaminoglycan comprising at least one of chondroitin 4-sulfate and chondroitin 6-sulfate; and
(d) at least ten substances selected from amino acids, α-biotin, $(NH_4)_6Mo_7O_{24}$, adenine, $AlCl_3$, biotin, $CaCl_2$, calcium pantothenate, choline chloride, $CoCl_2$, $CrK(SO_4)_2$, $CuSO_4$, D-Ca pantothenate, $EDTA.Na_2$, $EDTA.Na_3$, $Fe(NO_3)_3$, $FeSO_4$, folic acid, glucose, $H_2SeO_3$, HEPES, hypoxanthine, insulin human, KCl, linoleic acid, lipoic acid, $MgCl_2$, $MnCl_2$, $MnSO_4$, myo-inositol, $Na_2HPO_4$, $Na_2SeO_3$, $Na_2SiO_3$, NaCl, $NaH_2PO_4$, $NaHCO_3$, sodium pyruvate, sodium acetate, $NH_4VO_3$, $NiCl_2$, nicotinamide, phenol red, polysorbate 80, putrescine, putrescine 2HCl, pyridoxine HCl, pyridoxal HCl, riboflavin, $SnCl_2$, thiamine HCl, thymidine, vitamin $B_{12}$, and $ZnSO_4$, substances (a) to (c) being employed in a total amount of from about 0.015% to about 1% by weight, based on a total weight of the preparation, a weight ratio of substances (a) and (c) being from about 10:1 to about 8:1, and a weight ratio of substances (a) and (b) being from about 7:1 to about 2.5:1.

67. The preparation of claim 66, wherein the preparation comprises one or more skin cell culture media.

68. The preparation of claim 66, wherein the preparation further comprises a citrate buffer.

69. The preparation of claim 66, wherein the preparation further comprises at least one of Q10, alpha-glucosyl rutin, an alpha-hydroxy acid, Zn orotate, carnitine, creatine, and taurine.

70. The preparation of claim 66, wherein the preparation comprises at least about 50% by weight of water, based on a total weight of the preparation.

* * * * *